United States Patent
Xu

(10) Patent No.: US 11,542,311 B2
(45) Date of Patent: Jan. 3, 2023

(54) FUSION PROTEIN, PREPARATION METHOD THEREFOR AND APPLICATION THEREOF IN PREPARING OPHTHALMIC DISEASE TREATMENT, ANTI-INFLAMMATION AND ANTI-TUMOR MEDICAMENT

(71) Applicant: JIANGSU RONGTAI BIOTECH CO., LTD., Nanjing (CN)

(72) Inventor: Hanmei Xu, Nanjing (CN)

(73) Assignee: JIANGSU RONGTAI BIOTECH CO., LTD., Nanjing (CN)

( * ) Notice: Subject to any disclaimer, the term of this patent is extended or adjusted under 35 U.S.C. 154(b) by 198 days.

(21) Appl. No.: 16/496,397

(22) PCT Filed: Mar. 5, 2018

(86) PCT No.: PCT/CN2018/077968
§ 371 (c)(1),
(2) Date: Sep. 20, 2019

(87) PCT Pub. No.: WO2018/171411
PCT Pub. Date: Sep. 27, 2018

(65) Prior Publication Data
US 2021/0107960 A1    Apr. 15, 2021

(30) Foreign Application Priority Data
Mar. 20, 2017    (CN) .......................... 201710165208.2

(51) Int. Cl.
| | | |
|---|---|---|
| C07K 14/54 | (2006.01) | |
| A61P 27/02 | (2006.01) | |
| A61P 19/02 | (2006.01) | |
| A61P 29/00 | (2006.01) | |
| A61K 38/00 | (2006.01) | |
| C07K 14/475 | (2006.01) | |

(52) U.S. Cl.
CPC .......... *C07K 14/5406* (2013.01); *A61K 38/00* (2013.01); *A61P 19/02* (2018.01); *A61P 27/02* (2018.01); *A61P 29/00* (2018.01); *C07K 14/475* (2013.01); *C07K 2319/30* (2013.01)

(58) Field of Classification Search
None
See application file for complete search history.

(56) References Cited

U.S. PATENT DOCUMENTS 5,595,756 A  *  1/1997  Bally .................... A61K 9/1272
264/4.1

FOREIGN PATENT DOCUMENTS

| CN | 1235911 C | * | 1/2006 | ............. C07K 14/52 |
| CN | 105418769 A | * | 3/2016 | |
| CN | 105418769 B | * | 5/2020 | |
| WO | WO-2008101671 A2 | * | 8/2008 | ......... A61K 47/6813 |
| WO | WO 2008101671 A2 | | 8/2008 | |

OTHER PUBLICATIONS

Auerbach et al (Cancer and Metastasis Reviews, 2000, 19: 167-172) (Year: 2000).*
Gura T (Science, 1997, 278(5340): 1041-1042 (Year: 1997).*
HogenEsch et al (J Control Release. Dec. 10, 2012; 164(2): 183-186.) (Year: 2012).*
Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000, 10:398-400) (Year: 2000).*
Li et al (Cancer Gene Therapy (2004) 11, 363-370) (Year: 2004).*
Ma (Modern Drug Discovery 2004, 7(6) (Year: 2004).*
Steinman et al (Nat Med. Jan. 6, 2012;18(1):59-65) (Year: 2012).*
Blumberg et al (Nat Med.; 18(1): 35-41) (Year: 2015).*
Sporn et al, "Chemoprevention of Cancer," Carcinogenesis, vol. 21 (2000), 525-530 (Year: 2000).*
Xiaoying Chen Et. al. "Fusion Protein Linkers: Property, Design and Functionality" Advanced Drug Delivery Reviews, Sep. 29, 2012, p. 1357-1369.

* cited by examiner

*Primary Examiner* — Brian Gangle
*Assistant Examiner* — Andrea K McCollum
(74) *Attorney, Agent, or Firm* — Zhihua Han

(57) ABSTRACT

The invention discloses a fusion protein, a preparation method thereof and application thereof in preparing ophthalmic disease treatment, anti-inflammation and anti-tumor medicament, and belongs to the field of biopharmaceutical technology. The present invention uses a flexible (F) or rigid (R) linker to fuse two polypeptides to respectively obtain two bifunctional fusion proteins, namely two multi-functional fusion protein macromolecules obtained by linking antiangiogenesis polypeptides HM-3, interleukin 4 and immunoglobulin Fc fragments via an amino acid linker, which can improve drug efficacy, prolong half-life and enhance stability, has the characteristics of strong effect, low toxicity and the like, and can be used for the prevention and treatment of solid tumors and various types of inflammations and neovascular ophthalmic diseases. The fusion protein is expressed in a eukaryotic cell by a genetic engineering method and purified by affinity chromatography or the like.

5 Claims, 3 Drawing Sheets
Specification includes a Sequence Listing.

SEQUENCE LISTING

<160> NUMBER OF SEQ ID NOS: 7

<210> SEQ ID NO 1
<211> LENGTH: 404
<212> TYPE: PRT
<213> ORGANISM: Artificial Sequence
<220> FEATURE:
<223> OTHER INFORMATION: synthesized

<400> SEQUENCE: 1

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Ser Gly Gly Gly Gly
225                 230                 235                 240

Gly Ser His Lys Cys Asp Ile Thr Leu Gln Glu Ile Ile Lys Thr Leu
                245                 250                 255

Asn Ser Leu Thr Glu Gln Lys Thr Leu Cys Thr Glu Leu Thr Val Thr
            260                 265                 270

Asp Ile Phe Ala Ala Ser Lys Asn Thr Thr Glu Lys Glu Thr Phe Cys
        275                 280                 285

Arg Ala Ala Thr Val Leu Arg Gln Phe Tyr Ser His His Glu Lys Asp
    290                 295                 300

Thr Arg Cys Leu Gly Ala Thr Ala Gln Gln Phe His Arg His Lys Gln
305                 310                 315                 320

Leu Ile Arg Phe Leu Lys Arg Leu Asp Arg Asn Leu Trp Gly Leu Ala
                325                 330                 335

Gly Leu Asn Ser Cys Pro Val Lys Glu Ala Asn Gln Ser Thr Leu Glu
            340                 345                 350

Asn Phe Leu Glu Arg Leu Lys Thr Ile Met Asp Glu Lys Asp Ser Lys
```

```
                355                 360                 365
Cys Ser Ser Gly Gly Gly Ser Gly Gly Gly Ser Gly Gly
370                 375                 380
Gly Ser Ile Val Arg Arg Ala Asp Arg Ala Ala Val Pro Gly Gly Gly
385                 390                 395                 400
Gly Arg Gly Asp

<210> SEQ ID NO 2
<211> LENGTH: 418
<212> TYPE: PRT
<213> ORGANISM: Artificial Sequence
<220> FEATURE:
<223> OTHER INFORMATION: synthesized

<400> SEQUENCE: 2

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
    115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
    195                 200                 205
His Glu Ala Leu His Asn His Tyr Thr Gln Lys Ser Leu Ser Leu Ser
210                 215                 220
Pro Gly Lys Ala Glu Ala Ala Lys Glu Ala Ala Lys Glu Ala
225                 230                 235                 240
Ala Ala Lys Glu Ala Ala Lys Ala His Lys Cys Asp Ile Thr Leu
                245                 250                 255
Gln Glu Ile Ile Lys Thr Leu Asn Ser Leu Thr Glu Gln Lys Thr Leu
            260                 265                 270
Cys Thr Glu Leu Thr Val Thr Asp Ile Phe Ala Ala Ser Lys Asn Thr
    275                 280                 285
Thr Glu Lys Glu Thr Phe Cys Arg Ala Ala Thr Val Leu Arg Gln Phe
290                 295                 300
Tyr Ser His His Glu Lys Asp Thr Arg Cys Leu Gly Ala Thr Ala Gln
305                 310                 315                 320
```

```
Gln Phe His Arg His Lys Gln Leu Ile Arg Phe Leu Lys Arg Leu Asp
            325                 330                 335

Arg Asn Leu Trp Gly Leu Ala Gly Leu Asn Ser Cys Pro Val Lys Glu
        340                 345                 350

Ala Asn Gln Ser Thr Leu Glu Asn Phe Leu Glu Arg Leu Lys Thr Ile
    355                 360                 365

Met Asp Glu Lys Asp Ser Lys Cys Ser Ser Ala Glu Ala Ala Lys
370                 375                 380

Glu Ala Ala Lys Glu Ala Ala Lys Glu Ala Ala Lys Ala
385                 390                 395                 400

Ile Val Arg Arg Ala Asp Arg Ala Ala Val Pro Gly Gly Gly Gly Arg
            405                 410                 415

Gly Asp

<210> SEQ ID NO 3
<211> LENGTH: 1212
<212> TYPE: DNA
<213> ORGANISM: Artificial Sequence
<220> FEATURE:
<223> OTHER INFORMATION: synthesized

<400> SEQUENCE: 3
gacaagaccc acacatgccc tccttgtcct gctcctgagc tgctgggcgg accttccgtg      60
ttcctgtttc cccccaagcc caaggatacc ctcatgatca gcaggacccc cgaggtgaca     120
tgcgtggtgg tggatgtcag ccacgaggac cccgaggtga agttcaactg gtatgtcgac     180
ggcgtggagg tgcataacgc caagacaaag cccagggagg agcagtacaa cagcacatat     240
cgggtggtct ccgtgctcac cgtgctgcac caggattggc tcaacggcaa ggagtacaag     300
tgtaaggtgt ccaacaaggc cctccccgcc ccatcgaga agacaatcag caaggctaag     360
ggccaacctc gggagcccca agtctacacc ctgccccta gcaggacga gctcaccaag     420 aaccaggtca gcctgacatg tctggtgaag ggcttctacc ccagcgacat cgccgtggag     480
tgggaaagca acggacagcc cgagaacaac tacaagacca ccccccccgt gctggacagc     540
gacggcagct tcttcctgta cagcaagctg accgtcgata gagcaggtg gcagcagggc     600 aatgtgttta gctgctccgt gatgcacgag gccctgcata accactacac ccagaagagc     660
ctgagcctgt cccctggaaa gggaggcggc ggatccggcg gcggcggatc cggaggcggc     720
ggctcccata gtgcgacat caccctccag gaaatcatca agaccctgaa cagcctgacc     780
gagcagaaga ccctgtgcac cgagctgacc gtgaccgata tcttcgccgc ttccaagaac     840
accaccgaga aggagacctt ctgtagggcc gccaccgtcc tgaggcagtt ctatagccac     900
cacgagaaag acaccggtg tctgggcgcc acagctcagc agttccaccg gcacaagcag     960
ctgatccggt tcctcaagcg gctggatagg aacctgtggg gcctcgctgg cctgaacagc    1020
tgccccgtga aggaggctaa ccagagcacc ctggagaact tcctggaacg gctgaagacc    1080
atcatggacg aaaaagactc caagtgctcc agcgccggag gcggaagcgg cggcggaggc    1140
tccggaggcg gaggaagcat cgtgaggcgg gctgataggg ctgctgtgcc tggaggagga    1200
ggcaggggcg ac                                                        1212

<210> SEQ ID NO 4
<211> LENGTH: 1254
<212> TYPE: DNA
<213> ORGANISM: Artificial Sequence
<220> FEATURE:
```

<223> OTHER INFORMATION: synthesized

<400> SEQUENCE: 4

```
gacaaaaccc acacatgccc tccttgtccc gcccctgaac tgctcggcgg ccccagcgtc      60
ttcctgtttc ctcccaagcc taaagacacc ctgatgatca gccggacccc tgaggtcacc     120
tgcgtggtgg tcgatgtgag ccacgaggac cccgaggtga agttcaactg gtacgtcgac     180
ggagtggagg tccataatgc caagacaaag ccccggagg agcagtacaa ctccacctac      240
agggtggtca gcgtgctgac cgtcctccac caagactggc tcaatggcaa ggaatataaa     300
tgcaaggtga gcaacaaggc cctgcctgcc cccatcgaga agaccatctc caaggccaag     360
ggacagccca gggagcctca ggtgtacacc ctgcctccct ccagggacga gctgacaaag     420
aaccaggtga gcctcacatg cctggtgaag ggcttttatc ccagcgacat cgccgtcgag     480
tgggagagca cggccagcc tgagaacaac tacaagacca cccctcccgt cctcgactcc      540
gatggatcct tcttcctgta cagcaagctg accgtggata gagcaggtg gcagcagggc      600
aacgtgttct cctgtagcgt gatgcatgag gccctgcaca accattacac ccagaaatcc     660
ctgtccctgt ccctggcaa agccgaggcc gccgctaagg aagccgctgc caagaagcc       720
gctgccaagg aggccgctgc caaagcccac aagtgtgata tcacactgca ggagatcatc     780
aagaccctga atagcctcac cgagcagaag accctgtgca ccgaactgac cgtgaccgac     840
atctttgccg cctccaagaa taccaccgag aaggagacct ctgtcgggc tgccaccgtg      900
ctccggcagt tctacagcca ccacgagaag gacacccggt gcctgggagc taccgctcag     960
cagtttcacc ggcacaagca gctcatcagg ttcctgaaga ggctggatag gaacctgtgg    1020
ggcctggctg gcctgaattc ctgccccgtg aaggaggcta ccagtccac cctggagaat     1080
tttctggaga ggctgaagac catcatggat gagaaggaca gcaagtgttc ctccgctgaa    1140
gccgccgcta aggaggccgc cgctaaagag gctgccgcca ggaagctgc cgccaaagct    1200
atcgtgaggc gggccgacag ggctgctgtg cctggcggcg gcggcagggg cgac          1254
```

<210> SEQ ID NO 5
<211> LENGTH: 18
<212> TYPE: PRT
<213> ORGANISM: Artificial Sequence
<220> FEATURE:
<223> OTHER INFORMATION: synthesized

<400> SEQUENCE: 5

Ile Val Arg Arg Ala Asp Arg Ala Ala Val Pro Gly Gly Gly Gly Arg
1               5                   10                  15

Gly Asp

<210> SEQ ID NO 6
<211> LENGTH: 129
<212> TYPE: PRT
<213> ORGANISM: Artificial Sequence
<220> FEATURE:
<223> OTHER INFORMATION: synthesized

<400> SEQUENCE: 6

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

```
Ala Thr Val Leu Arg Gln Phe Tyr Ser His His Glu Lys Asp Thr Arg
         50                  55                  60

Cys Leu Gly Ala Thr Ala Gln Gln Phe His Arg His Lys Gln Leu Ile
 65                  70                  75                  80

Arg Phe Leu Lys Arg Leu Asp Arg Asn Leu Trp Gly Leu Ala Gly Leu
                 85                  90                  95

Asn Ser Cys Pro Val Lys Glu Ala Asn Gln Ser Thr Leu Glu Asn Phe
            100                 105                 110

Leu Glu Arg Leu Lys Thr Ile Met Asp Glu Lys Asp Ser Lys Cys Ser
            115                 120                 125

Ser

<210> SEQ ID NO 7
<211> LENGTH: 232
<212> TYPE: PRT
<213> ORGANISM: Artificial Sequence
<220> FEATURE:
<223> OTHER INFORMATION: synthesized

<400> SEQUENCE: 7

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230
```

FUSION PROTEIN, PREPARATION METHOD THEREFOR AND APPLICATION THEREOF IN PREPARING OPHTHALMIC DISEASE TREATMENT, ANTI-INFLAMMATION AND ANTI-TUMOR MEDICAMENT

CROSS REFERENCE TO RELATED APPLICATION

This application is a national stage application of International application number PCT/CN2018/077968, filed Mar. 5, 2018, titled "FUSION PROTEIN, PREPARATION METHOD THEREFOR AND APPLICATION THEREOF IN PREPARING OPHTHALMIC DISEASE TREATMENT, ANTI-INFLAMMATION AND ANTI-TUMOR MEDICAMENT," which claims the priority benefit of Chinese Patent Application No. 201710165208.2, filed on Mar. 30, 2017, which is hereby incorporated by reference in its entirety.

SEQUENCE LISTING

The content of the ASCII text file of the sequence listing named "NJZS0027US_ST25", which is 15 kb in size was created on and electronically submitted via EFS-Web Apr. 18, 2022, is incorporated herein by reference in its entirety.

BACKGROUND

Technical Field

The invention belongs to the field of biopharmaceutical technology, and more particularly relates to a fusion protein having anti-inflammatory and anti-tumor functions and therapeutic effects on ophthalmic diseases, and a preparation method and application thereof.

Related Art

Diseases such as arthritis, tumors, inflammations caused by bacteria, and ophthalmic diseases (such as Macular Degeneration or AMD) are called vascular-related diseases.

Arthritis-like inflammatory diseases refer to inflammatory diseases that occur in joints and surrounding tissues in human, and can be divided into dozens of types. There are more than 100 million arthritis patients in China, and the number of the patients is increasing. The clinical manifestations are redness, swelling, heat, pain, dysfunction and joint deformity, and in severe cases, joint disability is caused, affecting the quality of life of patients. These mainly include rheumatic arthritis, rheumatoid arthritis, osteoarthritis, gouty arthritis, ankylosing spondylitis, reactive arthritis, infectious arthritis, and the like. Among them, rheumatoid arthritis (RA) is one of the most common inflammatory joint diseases and major cause of disability in clinical. The incidence of RA is about 0.5% to 1.0% in the world, and about 0.4% in China. RA is a chronic systemic inflammatory disease whose cause is not yet clear, with chronic, symmetrical, multiple synovial arthritis and extra-articular lesions as the main clinical manifestations, and is an autoimmune inflammatory diseases. Patients often have pain and swelling in the hands or wrists (especially swelling of the back of the wrist) as the initial symptoms, and the symptoms are persistent and cannot be relieved. Although ordinary symptomatic treatment can alleviate the symptoms, the symptoms often relapse due to irregular or insufficient medication. When the disease progresses, obvious morning stiffness may occur, usually up to 1 hour or above, and it always gets worse constantly; at the same time, certain joint dysfunction occurs. Its basic pathological features are vasculitis and synovitis. Intra-articular synovial angiogenesis results in pannus, leading to thickening of the synovial membrane, increase of exudation, secretion of various cytokines, invasion of cartilage, and bone damage. It can also erode the muscle cavity, ligament, tendon sheath and muscles around it, which affects the stability of the joint, and is prone to joint malformation and dysfunction. Vasculitis can also invade all organs of the body, leading to systemic diseases. In the pathological process of arthritis, angiogenesis is a characteristic histological change. Neovascularization is accompanied by synovial hyperplasia and inflammatory cell infiltration, which is the basis of pannus formation and joint destruction. Articular cartilage, which should have no blood vessels, has formed new blood vessels due to some abnormal changes to erode cartilage, causing joint deformation or pain. New blood vessels cause abnormal changes to synovial tissue in patients with rheumatoid arthritis. Therefore, inhibition of neovascularization can alleviate or cure arthritis-like inflammatory diseases to a certain extent.

In recent years, the incidence and mortality of tumor in China have been increasing. Unrestricted growth, invasion, and metastasis are the signs and characteristics of malignant tumors, and are the main reasons of treatment failure and death. Therefore, controlling growth, invasion and metastasis of tumor is the main measure to improve the prognosis and survival. In 1971, Folkman first proposed the theory that tumor growth depends on angiogenesis. Tumor angiogenesis is the morphological basis of tumor growth and metastasis. It not only provides nutrition to tumors, but also inputs a large number of tumor cells to the host to cause tumor growth and metastasis. Most malignant solid tumors such as ovarian cancer, liver cancer, cervical cancer and breast cancer are vascular-dependent tumors. On the one hand, new blood vessels provide nutrition and oxygen for tumor growth, and on the other hand, they are important pathways for tumor metastasis. Therefore, inhibition of tumor angiogenesis is an important anticancer measure.

The pathogenesis of iris neovascular eye disease, choroidal neovascular eye disease, retinal neovascular eye disease and corneal neovascular eye disease in ophthalmic diseases is related to the excessive neovascularization, the inhibition of neovascularization is an important way to treat these diseases, while the proliferation and migration of endothelial cells is a key step for neovascularization. Angiogenesis inhibitors are a class of drugs that have attracted attention in the treatment of neovascular diseases in recent years, and thus blocking the neovascularization may become a new means of treating eye diseases in patients caused by angiogenesis in the eye. Among these angiogenesis inhibitors, angiostatin and endostatin are particularly attractive. Although these vascular inhibitors attract most attention, their defects are also very obvious. That is, the targets of the antiangiogenesis drugs such as endostatin and angiostatin are unclear, their specificity and selectivity for blood vessels are not good enough, and the effect is limited, resulting in a larger amount of drug used in the experiment. Therefore, a good anti-angiogenic drug should be selective for marker molecules of new blood vessels to achieve a guiding role for the new blood vessels, and to enhance the inhibitory effect of drugs on angiogenesis as a whole, so as to realize the effect of high-efficiency angiogenesis inhibition by using only a low dose of drugs. Avastin® (bevacizumab Vascular Endothelial Growth Factor (VEGF-A) Receptor Antagonist) has been successfully used in the treatment of eye diseases currently, but there is still no such drug independently developed in China. The inhibition of angiogenesis by integrin target of the present invention will be a new option for the treatment of such eye diseases.

In addition, arthritis-like inflammation, tumors, and ophthalmic diseases are vascular-related diseases. The growth and metastasis of tumor depend on new blood vessels; inflammation and angiogenesis are two pathological processes that are interrelated and co-developed; ophthalmic diseases such as age-related macular degeneration (AMD) are mainly characterized by choroidal neovascularization.

Neovascularization is highly regulated under normal physiological conditions and is an essential process in reproduction, embryonic development, tissue repair, and wound healing. Angiogenesis also occurs under various pathological conditions including: tumor growth and metastasis; inflammatory disorders such as rheumatoid arthritis, psoriasis, osteoarthritis, inflammatory bowel disease, Crohn's disease, ulcerative colitis and other inflammatory disorders.

Integrins are a class of receptors that are widely distributed on the cell surface, which can mediate the adhesion between cells and extracellular matrixes as well as the adhesion between cells and cells. They participate in angiogenesis by linking the interaction between intracellular cytoskeletal proteins and extracellular matrix molecules. Recently, at least eight integrins ($\alpha1\beta1$, $\alpha2\beta1$, $\alpha3\beta1$, $\alpha6\beta1$, $\alpha6\beta4$, $\alpha5\beta1$, $\alpha v\beta3$, $\alpha v\beta5$) are involved in angiogenesis, wherein $\alpha v\beta3$ plays an important role. $\alpha v\beta3$ can recognize the ARG-GLY-ASP (RGD) sequence in a ligand molecule, can be expressed in a variety of cell types and participates in physiological and pathological processes such as tumor angiogenesis, invasion, metastasis, inflammation, wound healing and coagulation in combination with multiple ligands during multicellular activity. Therefore, an RGD sequence-containing polypeptide can function as an integrin antagonist, and the RGD sequence can be used as a carrier which targeted transport to the neovascular endothelium to more efficiently treat neovascular diseases. Therefore, the antiangiogenesis polypeptide can prevent the delivery of oxygen and nutrition to the synovial membrane by inhibiting angiogenesis, and can also directly causes the blood vessel degeneration, thereby possibly inhibiting the synovial proliferation of the RA. The inhibition of neovascularization is an important way to treat these diseases, while the proliferation and migration of endothelial cells is a critical step for neovascularization.

SUMMARY

1. Problem to be Solved

In view of the problem that the existing polypeptide has a short half-life and a single target, the present invention provides a mammalian cell expression method, comprising linking two different active polypeptides and proteins in order to solve the following problems of improving the affinity of the polypeptide molecules to the target and the cytotoxicity of the polypeptide molecules, and enhancing the efficacy of the polypeptide molecules; overcoming the shortcomings of short half-life and frequent administration of the polypeptide molecules; and linking polypeptides targeting different targets via a linker to form a bifunctional protein molecule, and prolonging the half-life of the bifunctional protein, thereby laying a foundation for long-acting drug development.

2. Technical Solution

In order to solve the above problems, the technical solution adopted by the present invention is as follows.

A fusion protein comprises an antiangiogenesis polypeptide HM-3 sequence (SEQ ID NO: 5), an interleukin 4 (IL-4) sequence (SEQ ID NO: 6) and an Fc fragment of an antibody IgG1 (SEQ ID: 7), wherein the protein I is linked by a flexible (F) linker, and the polypeptides at both ends can change and move in order to obtain a better extensibility; the protein II is linked by a rigid (R) linker and the spatial displacement of the polypeptides at both ends cannot be easily formed, so that the functional domains at both ends do not affect each other. The structure diagram of protein I is shown in FIG. 1; the structure diagram of protein II is shown in FIG. 2.

Further, the amino acid sequence corresponding to the protein I is SEQ ID NO: 1; the amino acid sequence corresponding to the protein II is SEQ ID NO: 2.

For the genes encoding the above fusion proteins, the nucleic acid sequences encoding SEQ ID NO: 1, and SEQ ID NO: 2 are SEQ ID NO: 3 and SEQ ID NO: 4, respectively.

Use of the above fusion proteins in preparation of a medicament for treating inflammation, tumor, and ophthalmic disease is provided.

Further, the inflammation includes rheumatoid arthritis, osteoarthritis, gouty arthritis, ankylosing spondylitis, psoriatic arthritis, reactive arthritis, infectious arthritis and traumatic arthritis, systemic Lupus erythematosus, and psoriasis.

Further, the tumor includes gastric cancer, lung cancer, liver cancer, breast cancer, colon cancer, glioma, melanoma, and cervical cancer, as well as primary or secondary cancer, melanoma, and sarcoma originating from the head and neck, brain, thyroid, esophagus, pancreas, lung, liver, stomach, breast, kidney, gallbladder, colon or rectum, ovary, cervix, uterus, prostate, bladder, and testicle in human.

Further, the ophthalmic disease includes iris neovascular eye disease, choroidal neovascular eye disease, retinal neovascular eye disease, or corneal neovascular eye disease.

Further, the iris neovascular eye disease includes iris neovascular eye disease caused by neovascular glaucoma, diabetic retinopathy or central retinal vein occlusion; the choroidal neovascular eye disease includes age-related macular degeneration, central exudative chorioretinitis, ocular histoplasmosis syndrome or serpiginous choroidopathy; the retinal neovascular eye disease includes the retinal neovascular eye diseases associated with diabetes, tumor, retinal detachment, central retinal vein occlusion, retinal periphlebitis, systemic lupus erythematosus, Eales disease or Coat disease; the corneal neovascular eye disease includes the corneal neovascular eye diseases caused by cornea contacting a lens, as well as the corneal neovascular eye diseases caused by alkali and other chemical burns, corneal surgery, bacterial infection, chlamydial infection, viral infection or protozoal infection.

Further, the dosage form of the medicament is a capsule, a tablet, a pill, an injection, a nasal spray or an aerosol.

A preparation method of the above fusion proteins utilizes a method of expression by prokaryotic cells or eukaryotic cells and a method of purification.

3. Beneficial Effect

Compared with the prior art, the beneficial effects of the present invention are as follows.

(1) After extensive research, it is found that HM-3 has a good anti-angiogenic effect, but has a shorter half-life due to being a polypeptide; IL-4 molecule can promote the proliferation of T cells, B cells and macrophages to enhance the immune function of the body and achieve the function of killing tumors. On the one hand, the invention combines HM-3 and IL-4 molecule in order to achieve a dual anti-tumor effect, an anti-inflammatory effect and an anti-angiogenic effect, and at the same time, the immunity of the body can be improved. In addition, both HM-3 and interleukin 4 are polypeptides with a relatively small molecular weight, and their half-lives in the body is relatively short, usually up to about 30 minutes to about 2 hours. In the present invention, the Fc fragment sequence of IgG is introduced, and HM-3, IL-4 and the Fc fragment of IgG1 are linked together via a linker through a fusion protein construction technique to form a bifunctional fusion protein, which has a dual effect, i.e., the anti-angiogenic effect of HM-3 polypeptide and the anti-tumor effect of interleukin 4. More importantly, the addition of the Fc fragment significantly prolongs the half-lives of HM-3 and interleukin 4, and it is expected that the products will provide patients with a long-acting bifunctional drug in the treatment of related diseases after forming drugs, and such drug can be administered once a week or two weeks, or even once a month, so that the frequency of administration for patient is effectively reduced, the patient compliance is increased and the cost of treatment for patient is reduced.

(2) The problems of synthesis bottleneck of a polypeptide molecule having a large molecular weight and a complex structure, in particular a macromolecular polypeptide molecule having a secondary structure such as a disulfide bond and a high-order structure are solved; technical bottleneck of chemical synthesis difficulty and low yield of a large molecular weight polypeptide is overcome, and the production cost of the macromolecular polypeptide is significantly reduced; the expression of a polypeptide molecule by a living body cell such as a mammalian cell can form a correct high-order structure, and the affinity of the polypeptide molecule to the target molecule is superior to that of the chemically synthesized polypeptide molecule; the polypeptide molecule forms a fusion protein molecule with the Fc fragment of antibody IgG1, IgG2 or IgG4, and the Fc fragment of IgG is prevented from being degraded by a Fc receptor (FcRn)-mediated recycling mechanism, while the Fc fragment has a larger molecular weight and low renal clearance, so as to ensure that the half-life of the fusion protein is significantly longer than that of the polypeptide, and at the same time, the fusion protein formed by the fusion of the Fc fragment of IgG1 can increase the cytotoxicity of Antibody-Dependent Cell-Mediated Cytotoxicity (ADCC), and Complement Dependent Cytotoxicity (CDC), and can significantly increase the activity of anti-tumor molecules, and its anti-tumor effect is superior to that of polypeptide molecules; and the eukaryotic expression system was used to link the Fc fragment of the antibody to the HM-3 and IL-4 sequences by linker to prolong the half-lives of the functional proteins HM-3 and IL-4, and simultaneously link the polypeptides for two different targets to form a dual target fusion protein.

(3) The protein I (SEQ ID NO: 1) and the protein II (SEQ ID NO: 2) of the present invention are a class of recombinant protein drugs functioning as a integrin blocker and immunomodulator, which not only inhibit vascular proliferation but also have the functions of effectively regulating the immune system to inhibit tumor; the bifunctional fusion protein drug can significantly enhance the effect of the drug on inhibiting and killing tumor cells and inhibiting vascular proliferation compared with a single polypeptide drug. More importantly, the fusion protein can significantly prolong the half-life of the drug, improve the therapeutic effect of the drug, significantly improve the patient's drug compliance, and significantly reduce the cost of treatment for the patient. The fusion protein drug achieves the effect of treating arthritis, tumor and inflammation-related ophthalmic diseases through the above bifunctional action and prolonged half-life.

(4) The fusion protein sequence of the present invention includes an arginine-glycine-aspartate (RGD) sequence, the RGD sequence is an important ligand of integrin, and the RGD sequence-containing polypeptide Gly-Gly-Gly-Gly-Arg-Gly-Asp (SEQ ID NO: 8) can specifically recognize integrins, can effectively inhibit neovascularization, and can be used to treat tumor diseases, arthritis diseases and ophthalmic diseases. The present invention uses a flexible (S) or rigid (R) linker to fuse two polypeptides to obtain protein I and protein II, respectively, which can improve the efficacy, prolong the half-life, enhance stability, and have the characteristics of strong effect, low toxicity and the like.

(5) The fusion protein of the present invention can be targeted to the neovascular endothelium, and inhibit neovascularization to achieve the effects of preventing or treating vascular and inflammation-related diseases.

(6) The present invention has an effect of inhibiting various tumors in terms of anti-tumor, and it can be seen from the MTT assay results in Example 2 that the fusion protein I and fusion protein II can effectively inhibit proliferation of gastric cancer, lung cancer, liver cancer, breast cancer, melanoma, colon cancer, glioma and cervical cancer, the inhibition rate of melanoma, gastric cancer and human glioma reaches 50% or more at a concentration of 32 µg/mL; the inhibition rate of colon cancer cells reaches 40% or more, and the inhibition rate of cervical cancer cells reaches 50% or more at a concentration of 64 µg/mL;

(7) According to the present invention, in terms of inhibiting neovascularization, it can be clearly seen from the cell migration experiment of Example 3 that the inhibition of migration of HUVEC (Human Umbilical Vein Endothelial Cells) is significant at a concentration of 2 µg/mL, and the inhibition rate reaches 70% or more;

(8) According to the present invention, in terms of anti-inflammatory effects, it can be clearly seen from a series of verification model experiments of Examples 4-10 that fusion protein I and fusion protein II can significantly inhibit lymphocyte proliferation, inhibit IL-1β inflammatory factors production by macrophages, inhibit granuloma formation, reduce capillary permeability in model groups, inhibit ear swelling and toe swelling in model groups, and reduce the degree of chronic inflammation of adjuvant arthritis in rats;

(9) According to the present invention, in terms of the treatment of ophthalmic diseases, it can be seen from Examples 11-19 that fusion protein I and fusion protein II can significantly inhibit proliferation of human retinal vascular endothelial cells, inhibit the neovascularization of chicken embryo chorioallantoic membrane, inhibit the growth of corneal new blood vessels, inhibit the growth of iris new blood vessels in rabbits, promote the increase of choroidal blood flow in rabbit eyes, reduce the retinal neovascular plexus in OIR mice, inhibit neovascularization in oxygen-induced neonatal rat retinopathy model and has a certain therapeutic effect on diabetic retinopathy.

DETAILED DESCRIPTION

The invention is further described below in conjunction with specific examples.

Example 1

(I) Acquisition of Fusion Protein Gene and Construction of Expression Vector

The antiangiogenesis polypeptide HM-3 sequence is shown in SEQ ID NO: 5, the interleukin 4 sequence is shown in SEQ ID NO: 6, and the human immunoglobulin IgG1-Fc region (SEQ ID NO: 7) is linked to IL4DM-HM3 protein via different linker peptides Gly Gly Gly Gly Ser Gly Gly Gly Gly Ser Gly Gly Gly Gly Ser (SEQ ID NO: 9) flexible (F) linker and AlaGluAlaAlaAlaLysGluAlaAlaAlaLysGluAlaAlaAlaLysGluAlaAlaAlaLysAla (SEQ ID NO: 10) rigid (R) linker to design two novel Fc fusion proteins Fc-IL4DM-HM3, in which the amino acid sequence of the protein I constructed by the flexible (F) linker is shown in SEQ ID NO: 1, and the amino acid sequence of the protein II constructed by the rigid (R) linker is shown in SEQ ID NO: 2. According to the codon preference in CHO cell, the coding sequences of two novel Fc fusion proteins Fc-IL4DM-HM3 are optimized, in which NheI cleavage sites, Kozak sequences, and signal peptides are introduced at the 3' end, and XhoI cleavage sites are introduced at the 5' end, thereby obtaining the following DNA sequences SEQ ID NO: 3 and SEQ ID NO: 4 by a whole gene synthesis method.

The DNA sequences of the above 2 fusion proteins Fc-IL4DM-HM3 were synthesized by a commissioned biotechnology company, ligated to a pUC57 vector to form a cloning vector, and stored in *E. coli* DH5a to form a clone strain. The two fusion proteins all used pcDNA3.4/MCS(+) as the expression vectors, and the vector construction processes are completely identical. Therefore, Fc-IL4DM-HM3-1 is taken as an example, and the experimental procedures were as follows.

1. Under sterile conditions, the Fc-IL4DM-HM3-1 clone strain sent by the biotechnology company was picked up from the surface of the bacteria *penetrans* and inoculated into two tubes containing 5 mL of Amp-resistant LB medium at 37° C., 120 rpm under shaking overnight.

2. After the culture of the bacteria solution in the two tubes, 2.5 mL of sterile 60% glycerol was added in one tube, mixed well, and then charged into sterile centrifuge tubes, with 1 mL per tube, to prepare glycerin tubes, which were frozen and stored at −80° C. The bacteria solution in the other tube was centrifuged at 12,000 rpm for 1 min to collect thalli, and a cloning vector of Fc-IL4DM-HM3-1 was extracted by using a conventional commercial plasmid mini-prep kit.

Figure 1:
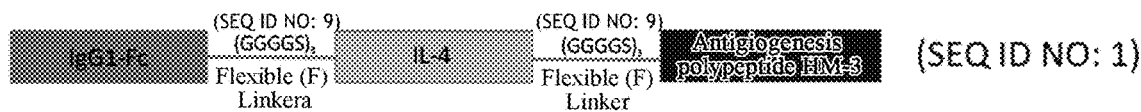
FIG. 1 is a structural schematic diagram of a protein corresponding to SEQ ID NO: 1 according to the present invention.
Figure 2:
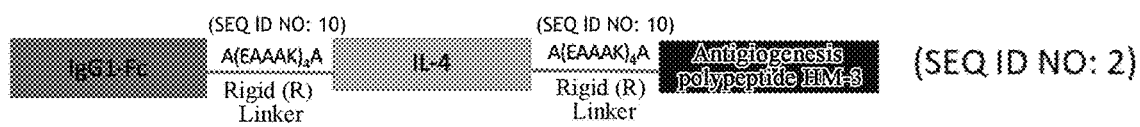
FIG. 2 is a structural schematic diagram of a protein corresponding to SEQ ID NO: 2 according to the present invention.
Figure 3:
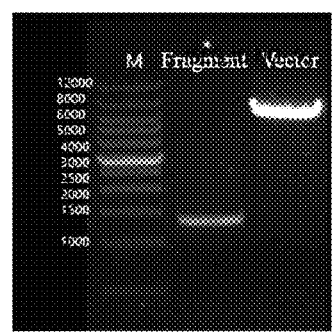
FIG. 3 is an electrophoretogram of a fragment obtained by gel extraction of Fc-IL4DM-HM3-1 and expression vector pcDNA3.4/MCS(+) according to the present invention.

3. The restriction endonuclease NheI/XhoI was used to perform double enzyme digestion of the Fc-IL4DM-HM3-1 cloning vector and the expression vector pcDNA3.4/MCS(+), and the inserted fragment Fc-IL4DM-HM3-1 having cohesive ends and the expression vector pcDNA3.4/MCS(+) were separated by horizontal nucleic acid electrophoresis and recovered by using a commercial DNA gel extraction kit. The DNA fragment recovery results are shown in FIG. 3.

4. Using the T4 ligase, the ligation between the inserted fragment Fc-IL4DM-HM3-1 and the expression vector pcDNA3.4/MCS(+) obtained by gel extraction were carried out at 16° C. according to the molar ratio of inserted fragment to vector of 1:5 for 16 h.

5. 20 uL of DNA ligation was added to 100 uL of freshly thawed *E. coli* TOP10 competent cells, mixed gently, and placed in an ice bath for 30 min. After being heat-shocked at 42° C. for 45 s, the mixture was quickly placed in an ice bath for 2 to 3 minutes. 900 uL of non-resistant LB medium was added to the mixture, and cultured at 37° C. for 1 h under shaking. The mixture was centrifuged at 4500 rpm for 1 min at 4° C., 900 uL of supernatant was discarded under sterile conditions, the remaining bacterial solution and the precipitated thalli were mixed evenly via gentle blowing-suction, all of which was aspirated by a pipette, and coated to an Amp-resistant LB solid plate and statically cultured at 37° C. for 12 h.

6. 20 single colonies were picked up and inoculated in a tube containing 5 mL of Amp-resistant LB medium, and cultured at 37° C., 120 rpm under shaking overnight.

Figure 4:
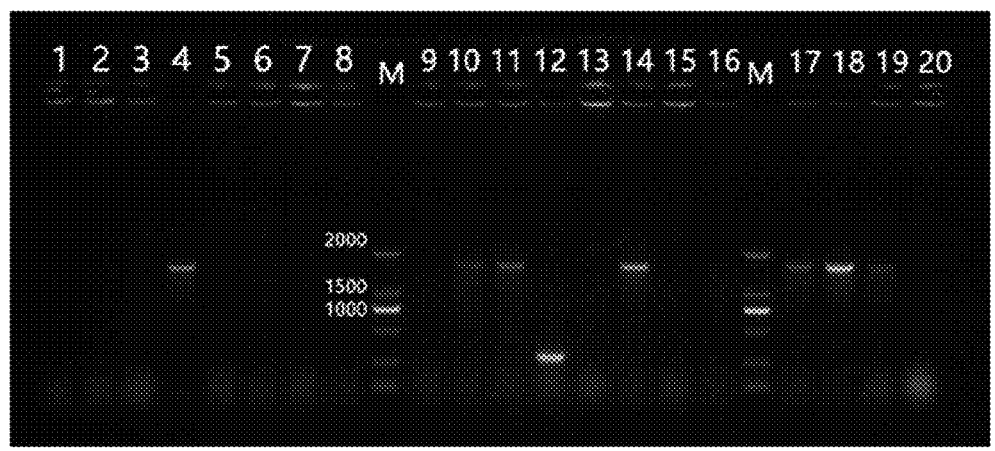
FIG. 4 is a diagram showing the results of PCR verification of bacterial liquid according to the present invention.

7. Among the strains inoculated in the previous step, each of normally growing strains was stored in 3 glycerol tubes. At the same time, each strain was tested by bacterial PCR verification (see FIG. 4), positive clones were screened, and the preserved glycerol tubes were sent to the biotechnology company for sequencing verification. The correct expression vector was finally obtained.

8. The glycerol tubes preserving the strain having correct sequencing was taken out, inoculated into a 250 mL shake flask containing 30 mL of Amp-resistant LB medium, incubated at 37° C., 120 rpm overnight, stored in 20 glycerol tubes, which were stored at −80° C. At this point, the construction of the Fc-IL4DM-HM3-1 expression vector was finished.

(II) Expression of Fusion Protein

Transient transfection is one of the ways to introduce DNA into eukaryotic cells. In transient transfection, recombinant DNA is introduced into highly infectious cell lines to obtain transient but high levels of expression of target gene. Enough proteins can be obtained for experiments in a short period of time, saving cell screening time in stable transfection.

The Expi293 Expression System is used to express two novel fusion proteins Fc-IL4DM-HM3. Since the expression processes of the fusion proteins are completely identical, the Fc-IL4DM-HM3-1 is used as an example. The experimental procedures are as follows.

1. Plasmid Preparation.

A glycerol tube preserving strain with Fc-IL4DM-HM3-1 expression vector was taken from a refrigerator at −80° C., inoculated into a 2 L shake flask containing 500 mL of Amp-resistant LB medium, and cultured at 37° C., 160 rpm under shaking overnight.

After the completion of the culture, the mixture was centrifuged at 5000 g for 5 min to collect thalli, and the plasmid was extracted using a commercial EndoFree Plasmid Maxi Kit. The plasmid concentration was controlled to be 1 mg/mL or above (if it is lower than this concentration, concentration is required), and then sterilized by filtration using a sterile 0.22 μm pore size filter to complete plasmid preparation.

2. Early-Stage Preparation of Transient Transfection of Cells

The 293F cells used for transfection were passaged at a cell density of $0.4*10^6$ cells/mL for every four days from the day of thawing, and at least three passages were performed, followed by the transient transfection. During the passage, the passage volume was expanded as needed based on the volume of the final transfection medium.

3. Transient Transfection (Taking 30 mL Transfection Volume as an Example, Multiply as Needed)

(1) One day before the experiment, $6*10^7$ live cells were inoculated into 30 mL Expi293 Expression Medium, and cultured at 37° C., 8% $CO_2$, 125 rpm under shaking.

(2) On the day of the experiment, the cells cultured on the previous day were counted firstly, the cell density should be $3-5*10^6$ cells/mL, and the viability was greater than 95%.

(3) $7.5*10^7$ cells were aspirated into a new 125 mL Erlenmeyer flask and the preheated Expi293 Expression Medium was added to 25.5 mL.

(4) Preparation of plasmid-transfection reagent mixture a. 30 μg of plasmid DNA was re-dissolved in 1.5 mL of Opti-MEM I Reduced Serum Medium and mixed gently.

b. 81 μL of ExpiFectamine 293 Reagent was added to Opti-MEM I Reduced Serum Medium to a volume of 1.5 mL. The mixture was gently mixed and incubated for 5 min at room temperature (long incubation period affects conversion efficiency).

c. The above two solutions were mixed gently, and incubated for 20-30 min at room temperature to complete the preparation of the plasmid-transfection reagent mixture.

(5) 3 mL of plasmid-transfection reagent mixture was added to the cell culture liquid of step 3 to 28.5 mL in total.

(6) The mixture was cultured at 37° C., 8% $CO_2$, 125 rpm under shaking for 20 h.

(7) 150 μL of ExpiFectamine 293 Transfection Enhancer 1 and 1.5 mL of ExpiFectamine 293 Transfection Enhancer 2 were added. At this point, the total volume was 30 mL.

(8) The mixture was cultured at 37° C., 8% $CO_2$, 125 rpm under shaking. The culture was terminated after 6 days and protein purification was carried out.

(III) Purification of Fusion Protein

Protein A is a cell-wall protein isolated from *Staphylococcus aureus*, which binds to mammalian IgG mainly through the Fc fragment and has very high specificity and binding ability, and is widely used for purification of IgG antibodies and IgG-Fc fusion proteins. The two novel fusion proteins Fc-IL4DM-HM3-1 have IgG-Fc fragments and thus the purification processes are completely identical. Therefore, Fc-IL4DM-HM3-1 produced by transient transfection at 1.6 L scale is used as an example. The experimental procedures are as follows.

1. Sample pretreatment: 1.6 L of transiently transfected cell culture liquid after culture termination was centrifuged at 7500 rpm for 20 min at 4° C., and the supernatant obtained was about 1.46 L for the next protein A capture.

Figure 5:
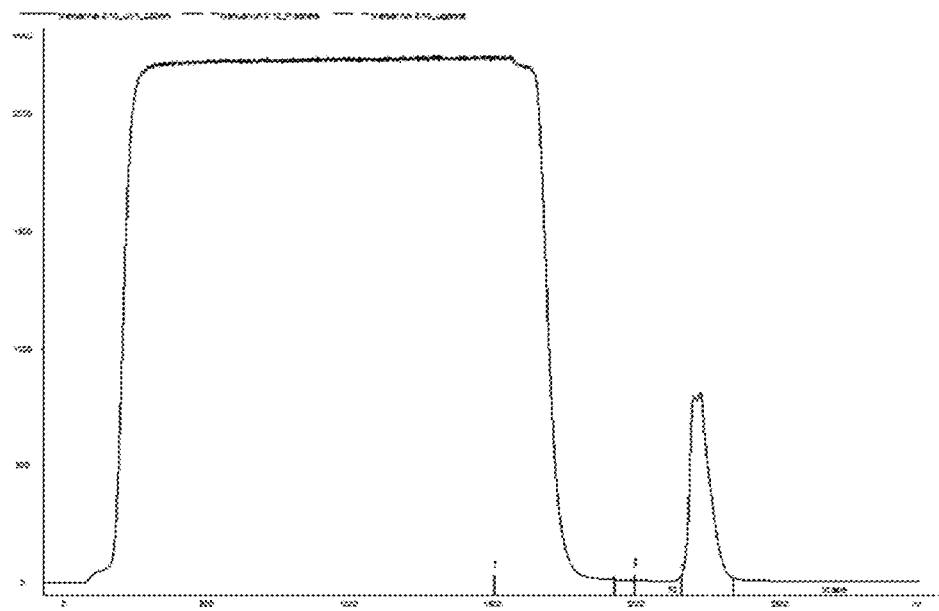
FIG. 5 is a diagram showing the results of capture of fusion protein according to the present invention.

2. Affinity capture of target protein (see FIG. 5)

The column information is as follows

| Packing | Mabselect SuRe |
|---|---|
| Column | XK50/20 |
| Column height (cm) | 10 |
| Cross-sectional area of column (cm$^2$) | 19.62 |
| Packing volume (mL) | 196.2 | a. The sterilization was first performed with 500 mL of 0.2 M NaOH at a flow rate of 10 mL/min.

b. The column was equilibrated with 20 mM PB, and 0.15 M NaCl, pH 7.0, the volume was about 1000 mL, and the flow rate was 20 mL/min.

c. Loading: the sample was pre-adjusted to a neutral pH, and the flow rate was 20 mL/min.

d. The column was washed with 20 mM PB and 0.15 M NaCl, pH 7.0, the volume was about 800 mL, and the flow rate was 20 mL/min.

e. The target protein was eluted with 50 mM citric acid-sodium citrate, and 0.15 M NaCL, pH 3.0, collection was started at onset 20 mAu and stopped at post-peak 20 mAu; and the flow rate was flow rate 20 mL/min.

f. The column was finally washed with 500 mL of 0.2 M NaOH, rinsed with water to neutral, and the column was stored with 20% ethanol.

Figure 6:
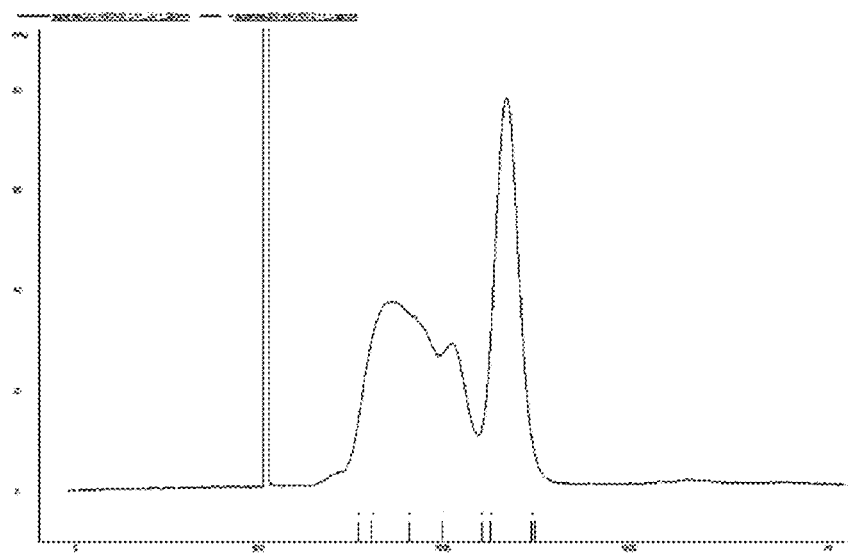
FIG. 6 is a diagram showing the fine purification of fusion protein according to the present invention.

3. Further separation and purification by gel chromatography (FIG. 6)

Column Parameters:

| Packing | Superdex200 |
|---|---|
| Column | XK50/60 |
| Column height (cm) | 58 |
| Cross-sectional area of column (cm$^2$) | 19.62 |
| Packing volume (mL) | 1138 |
| Flow rate | ml/min |
| Loading | 1-10% loading volume | a. The sterilization was performed with 300 mL of 0.5 M NaOH at a flow rate of 10 mL/min, and followed by rinsed with ultrapure water to about neutral.

b. The column was equilibrated with a PBS buffer, pH 7.4, the equilibrium volume was about 1500 mL, and the flow rate was 10 mL/min.

c. Loading: the sample was a protein A eluent, and the loading volume was 40 mL.

d. The sample was collected, peak 3 was the target protein peak, for the collection of peak 3, collection was started at onset 10 mAu peak and stopped at post-peak 10 mAu.

e. Finally, the column was stored with 0.1 M NaOH and the flow rate was 10 mL/min.

Figure 7:
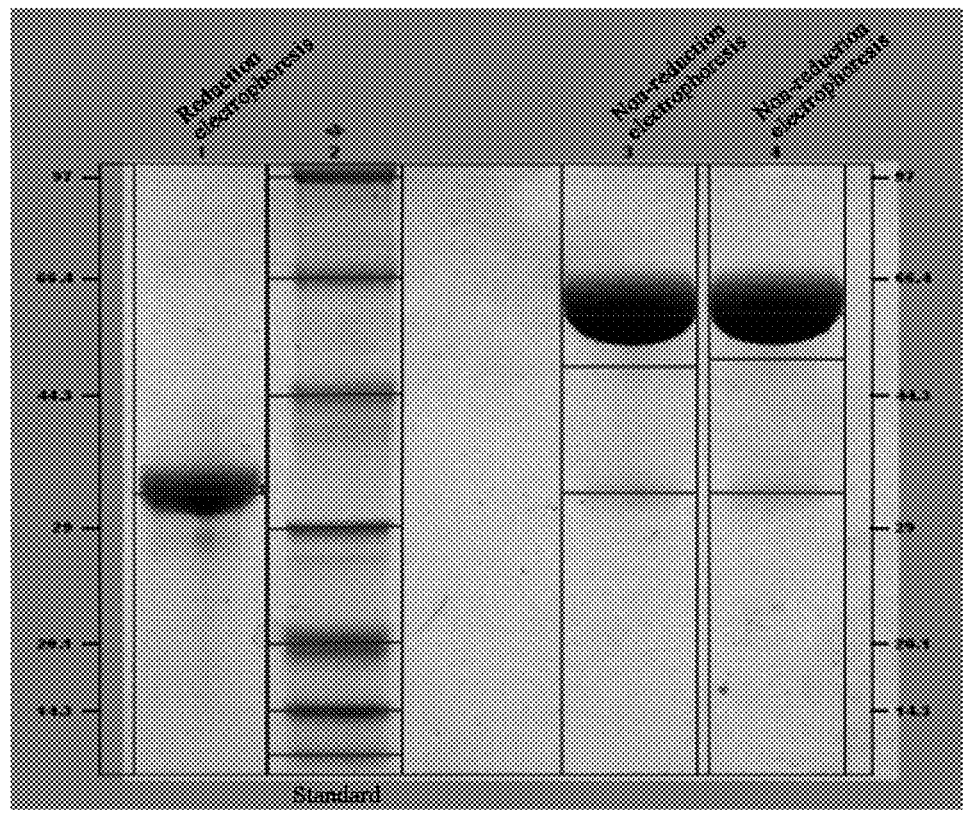
FIG. 7 is a diagram showing the results of analysis of a fusion protein sample by an SDS-PAGE method according to the present invention.
Figure 8:
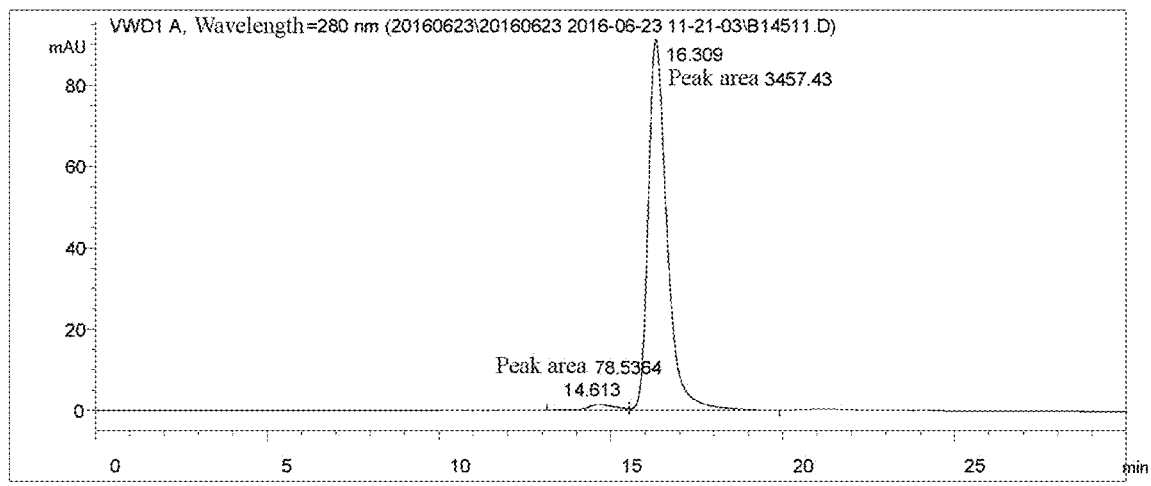
FIG. 8 is a diagram showing the results of analysis of a fusion protein sample by HPLC according to the present invention.

4. Ultrafiltration concentration of sample: the samples of peak 3 were combined and subjected to ultrafiltration concentration. A 10 kDa ultrafiltration membrane was selected, and the samples were concentrated to a target protein concentration of more than 5 mg/mL, and then the samples were charged and stored in a refrigerator at −80° C. The initial concentration was about 0.29 mg/mL, and the samples were finally concentrated to 27 mL, and the concentration was about 5.53 mg/mL; the sample were charged and cryopreserved. At the same time, samples were subjected to release detection by SDS-PAGE and HPLC (FIG. 7 and FIG. 8), and then used for druggability evaluation studies.

Example 2

Inhibitory Effect of Fusion Protein on Proliferation of Various Tumor Cells

The MTT assay was used to detect the inhibitory effect of the integrin blocker fusion protein obtained in Example 1 on the proliferation of various tumor cells, including melanoma cell B16F10, gastric cancer cell MGC-803, lung cancer cell A549, liver cancer cell Hep-G2, breast cancer cell MDA-MB-231, colon cancer cell HCT-116, human glioma U87, and cervical cancer cell Hela.

The tumor cells were cultured in a 5% $CO_2$ incubator at 37° C. to a density of 90% or more, and collected by trypsinization. The cells were resuspended in the culture liquid and counted under a microscope. The cell concentration was adjusted to $3.0×10^4$ cells/mL. The cell suspension was inoculated into a 96-well plate, 100 μL per well, and cultured overnight in a 5% $CO_2$ incubator at 37° C. The fusion proteins I, II, and the positive drug Taxol were diluted with the culture liquid to respective predetermined concentrations. After the cells were fully adhered, each dilution was added to a 96-well plate, 100 μL per well, respectively. The integrin blocker fusion proteins I and II were added as an administration group, Taxol was used as a positive control group, and the culture liquid without any drug was used as a blank control group, and incubated in an 5% $CO_2$ incubator at 37° C. for 48 hours. 20 μL of 5 mg/mL MTT was added to each well of a 96-well plate, and incubation was continued for 4 hours. The medium was aspirated and 100 μL of DMSO per well were added to dissolve. The absorbance was measured at 570 nm with a microplate reader with a reference wavelength of 630 nm, and the proliferation inhibition (PI) was calculated. The formula is as follows:

$$PI(\%) = 1 - \frac{N_{test}}{N_{control}} \times 100\%$$

where $N_{test}$ is the OD value of the test group and $N_{control}$ is the OD value of the blank control group.

Data Statistics:

The test was repeated 5 times independently. The results obtained from the test were calculated as mean±SD, and statistical t-test was performed. P<0.05 was considered as significant difference, and P<0.01 was considered as an extremely significant difference. The experimental results are shown in Tables 1-8.

TABLE 1

Inhibitory effect of fusion protein I and II on proliferation of melanoma cell B16F10

| Group (n = 5) | Dose (μg/mL) | A570 nm/A630 nm | PI (%) |
|---|---|---|---|
| Protein I | 1 | 1.1081 ± 0.0159 | 11.75% |
| | 2 | 1.0012 ± 0.0786 | 20.26% |
| | 4 | 0.8611 ± 0.0643* | 31.42% |
| | 8 | 0.6974 ± 0.0421** | 44.46% |
| | 16 | 0.5234 ± 0.0769** | 58.31% |
| | 32 | 0.4331 ± 0.0591** | 65.51% |
| | 64 | 0.3032 ± 0.0279** | 75.85% |
| | 128 | 0.1954 ± 0.0499** | 84.44% |
| | 256 | 0.0834 ± 0.0334** | 93.36% |

TABLE 1-continued

Inhibitory effect of fusion protein I and II on proliferation of melanoma cell B16F10

| Group (n = 5) | Dose (μg/mL) | A570 nm/A630 nm | PI (%) |
|---|---|---|---|
| Protein II | 1 | 1.1154 ± 0.0382 | 11.17% |
| | 2 | 1.0259 ± 0.0232 | 18.29% |
| | 4 | 0.8991 ± 0.0725* | 28.39% |
| | 8 | 0.7251 ± 0.0429** | 42.25% |
| | 16 | 0.6411 ± 0.0659** | 48.94% |
| | 32 | 0.5034 ± 0.0279** | 59.91% |
| | 64 | 0.3865 ± 0.0189** | 69.22% |
| | 128 | 0.2939 ± 0.0319** | 76.59% |
| | 256 | 0.1749 ± 0.0209** | 85.07% |
| Taxol | 5 | 0.6011 ± 0.0144** | 52.13% |
| control | — | 1.2556 ± 0.0411 | 0.00% |

*P < 0.05,
**P < 0.01 vs control.

The results showed that fusion protein I and protein II could effectively inhibit melanoma cell B16F10, and the inhibition rate reached 40% or more at a concentration of 8 μg/mL.

TABLE 2

Inhibitory effect of protein I and protein II on proliferation of gastric cancer cell MGC-803

| Group (n = 5) | Dose (μg/mL) | A570 nm/A630 nm | PI (%) |
|---|---|---|---|
| Protein I | 1 | 0.8701 ± 0.0456 | 8.92% |
| | 2 | 0.8301 ± 0.0343 | 13.11% |
| | 4 | 0.7531 ± 0.0236* | 21.17% |
| | 8 | 0.6859 ± 0.0395 | 28.20% |
| | 16 | 0.5692 ± 0.0222* | 40.42% |
| | 32 | 0.4365 ± 0.0239** | 54.31% |
| | 64 | 0.3068 ± 0.0398** | 67.88% |
| | 128 | 0.1696 ± 0.0431** | 82.25% |
| | 256 | 0.0945 ± 0.0249** | 90.11% |
| Protein II | 1 | 0.8821 ± 0.0306 | 7.66% |
| | 2 | 0.7852 ± 0.0125 | 17.81% |
| | 4 | 0.7049 ± 0.0323* | 26.21% |
| | 8 | 0.7421 ± 0.0460 | 22.32% |
| | 16 | 0.6342 ± 0.0302* | 33.61% |
| | 32 | 0.4523 ± 0.0271** | 52.65% |
| | 64 | 0.3796 ± 0.0133** | 60.26% |
| | 128 | 0.2276 ± 0.0511** | 76.18% |
| | 256 | 0.1112 ± 0.0115** | 88.36% |
| Taxol | 5 | 0.4146 ± 0.0186** | 56.60% |
| control | — | 0.9553 ± 0.0113 | 0.00% |

*P < 0.05
**P < 0.01 vs control.

The results showed that fusion protein I and protein II could effectively inhibit gastric cancer cell MGC-803, and the inhibition rate reached 50% or more at a concentration of 32 μg/mL.

TABLE 3

Inhibitory effect of protein I and protein II on proliferation of lung cancer cell A549

| Group (n = 5) | Dose (μg/mL) | A570 nm/A630 nm | PI (%) |
|---|---|---|---|
| Protein I | 1 | 0.6466 ± 0.0503 | 4.14% |
| | 2 | 0.5947 ± 0.0173 | 11.83% |
| | 4 | 0.5603 ± 0.0416 | 16.93% |
| | 8 | 0.5225 ± 0.0293* | 22.54% |
| | 16 | 0.4866 ± 0.0299* | 27.86% |
| | 32 | 0.4395 ± 0.0124** | 34.84% |
| | 64 | 0.3837 ± 0.0396** | 43.11% |
| | 128 | 0.3263 ± 0.0218** | 51.62% |
| | 256 | 0.2609 ± 0.0265** | 61.32% |

TABLE 3-continued

Inhibitory effect of protein I and protein II on proliferation of lung cancer cell A549

| Group (n = 5) | Dose (μg/mL) | A570 nm/A630 nm | PI (%) |
|---|---|---|---|
| Protein II | 1 | 0.6215 ± 0.0196 | 7.86% |
|  | 2 | 0.6051 ± 0.0125 | 10.29% |
|  | 4 | 0.5833 ± 0.0339 | 13.52% |
|  | 8 | 0.5516 ± 0.0313* | 18.22% |
|  | 16 | 0.5067 ± 0.0241* | 24.88% |
|  | 32 | 0.4698 ± 0.0178** | 30.35% |
|  | 64 | 0.4259 ± 0.0336** | 36.86% |
|  | 128 | 0.3509 ± 0.0116** | 47.98% |
|  | 256 | 0.2775 ± 0.0267** | 58.86% |
| Taxol | 5 | 0.3226 ± 0.0309** | 52.17% |
| control | — | 0.6745 ± 0.0231 | 0.00% |

*P < 0.05
**P < 0.01 vs control.

The results showed that fusion protein I and protein II could effectively inhibit lung cancer cell A549, and the inhibition rate reached 45% or more at a concentration of 128 μg/mL.

TABLE 4

Inhibitory effect of protein I and protein II on proliferation of liver cancer cell Hep-G2

| Group (n = 5) | Dose (μg/mL) | A570 nm/A630 nm | PI (%) |
|---|---|---|---|
| Protein I | 1 | 0.9884 ± 0.0424 | 3.77% |
|  | 2 | 0.9666 ± 0.0276 | 5.89% |
|  | 4 | 0.9169 ± 0.0253 | 10.73% |
|  | 8 | 0.8793 ± 0.0133* | 14.39% |
|  | 16 | 0.7989 ± 0.0305* | 22.22% |
|  | 32 | 0.7564 ± 0.0114* | 26.36% |
|  | 64 | 0.6915 ± 0.0242** | 32.67% |
|  | 128 | 0.6558 ± 0.0189** | 36.15% |
|  | 256 | 0.6024 ± 0.0134** | 41.35% |
| Protein II | 1 | 0.9816 ± 0.0382 | 4.43% |
|  | 2 | 0.9555 ± 0.0197 | 6.97% |
|  | 4 | 0.9133 ± 0.0384 | 11.08% |
|  | 8 | 0.8856 ± 0.0115* | 13.78% |
|  | 16 | 0.8076 ± 0.0411* | 21.37% |
|  | 32 | 0.7622 ± 0.0175* | 25.79% |
|  | 64 | 0.7116 ± 0.0369** | 30.72% |
|  | 128 | 0.6809 ± 0.0216** | 33.71% |
|  | 256 | 0.6108 ± 0.0468** | 40.53% |
| Taxol | 5 | 0.4257 ± 0.0099** | 58.55% |
| control | — | 1.0271 ± 0.0531 | 0.00% |

*P < 0.05
**P < 0.01 vs control.

The results showed that fusion protein I and protein II had certain inhibitory effects on liver cancer cell Hep-G2, and the inhibition rate increased along with the increase of concentration.

TABLE 5

Inhibitory effect of protein I and protein II on proliferation of breast cancer cell MDA-MB-231

| Group (n = 5) | Dose (μg/mL) | A570 nm/A630 nm | PI (%) |
|---|---|---|---|
| Protein I | 1 | 0.8133 ± 0.0262 | 5.77% |
|  | 2 | 0.7992 ± 0.0250 | 7.40% |
|  | 4 | 0.7798 ± 0.0409 | 9.65% |
|  | 8 | 0.7371 ± 0.0378* | 14.60% |
|  | 16 | 0.6706 ± 0.0185* | 22.30% |
|  | 32 | 0.6109 ± 0.0130* | 29.22% |
|  | 64 | 0.5499 ± 0.0186** | 36.29% |
|  | 128 | 0.4982 ± 0.0326** | 42.28% |
|  | 256 | 0.4410 ± 0.0171** | 48.91% |

TABLE 5-continued

Inhibitory effect of protein I and protein II on proliferation of breast cancer cell MDA-MB-231

| Group (n = 5) | Dose (μg/mL) | A570 nm/A630 nm | PI (%) |
|---|---|---|---|
| Protein II | 1 | 0.8213 ± 0.0202 | 4.84% |
|  | 2 | 0.8008 ± 0.0199 | 7.22% |
|  | 4 | 0.7805 ± 0.0430 | 9.57% |
|  | 8 | 0.7219 ± 0.0333* | 16.36% |
|  | 16 | 0.6779 ± 0.0130* | 21.46% |
|  | 32 | 0.6186 ± 0.0160* | 28.33% |
|  | 64 | 0.5555 ± 0.0331** | 35.70% |
|  | 128 | 0.5011 ± 0.0275** | 41.94% |
|  | 256 | 0.4476 ± 0.0282** | 48.06% |
| Taxol | 5 | 0.4071 ± 0.0301** | 52.83% |
| control | — | 0.8631 ± 0.0409 | 0.00% |

*P < 0.05
**P < 0.01 vs control.

The results showed that fusion protein I and protein II could effectively inhibit breast cancer cell MDA-MB-231, and the inhibition rate reached 40% or more at a concentration of 128 μg/mL.

TABLE 6

Inhibitory effect of protein I and protein II on proliferation of colon cancer cell HCT-116

| Group (n = 5) | Dose (μg/mL) | A570 nm/A630 nm | PI (%) |
|---|---|---|---|
| Protein I | 1 | 0.6640 ± 0.0246 | 2.40% |
|  | 2 | 0.6412 ± 0.0181 | 5.75% |
|  | 4 | 0.6089 ± 0.0131 | 10.50% |
|  | 8 | 0.5503 ± 0.0319* | 19.11% |
|  | 16 | 0.5285 ± 0.0222* | 22.31% |
|  | 32 | 0.4529 ± 0.0190** | 33.43% |
|  | 64 | 0.3726 ± 0.0190** | 45.23% |
|  | 128 | 0.2826 ± 0.0151** | 58.46% |
|  | 256 | 0.2071 ± 0.0271** | 69.56% |
| Protein II | 1 | 0.6610 ± 0.0280 | 2.84% |
|  | 2 | 0.6440 ± 0.0143 | 5.34% |
|  | 4 | 0.6112 ± 0.0495 | 10.16% |
|  | 8 | 0.5615 ± 0.0125* | 17.46% |
|  | 16 | 0.5416 ± 0.0375* | 20.39% |
|  | 32 | 0.4889 ± 0.0109** | 28.13% |
|  | 64 | 0.4000 ± 0.0020** | 41.20% |
|  | 128 | 0.3126 ± 0.0255** | 54.05% |
|  | 256 | 0.2324 ± 0.0283** | 65.84% |
| Taxol | 5 | 0.2098 ± 0.0164** | 69.16% |
| control | — | 0.6803 ± 0.0441 | 0.00% |

*P < 0.05
**P < 0.01 vs control.

The results showed that fusion protein I and protein II could effectively inhibit colon cancer cell HCT-116, and the inhibition rate reached 40% or more at a concentration of 64 μg/mL.

TABLE 7

Inhibitory effect of protein I and protein II on proliferation of human glioma U87

| Group (n = 5) | Dose (μg/mL) | A570 nm/A630 nm | PI (%) |
|---|---|---|---|
| Protein I | 1 | 0.7370 ± 0.0190 | 4.52% |
|  | 2 | 0.6916 ± 0.0275 | 10.40% |
|  | 4 | 0.6209 ± 0.0314* | 19.56% |
|  | 8 | 0.5377 ± 0.0212** | 30.34% |
|  | 16 | 0.4788 ± 0.0366** | 37.97% |
|  | 32 | 0.3520 ± 0.0223** | 54.40% |
|  | 64 | 0.2330 ± 0.0112** | 69.81% |
|  | 128 | 0.1346 ± 0.0283** | 82.56% |
|  | 256 | 0.0820 ± 0.0230** | 89.38% |

TABLE 7-continued

Inhibitory effect of protein I and protein II on proliferation of human glioma U87

| Group (n = 5) | Dose (μg/mL) | A570 nm/A630 nm | PI (%) |
|---|---|---|---|
| Protein II | 1 | 0.7480 ± 0.0299 | 3.10% |
| | 2 | 0.7042 ± 0.0166 | 8.77% |
| | 4 | 0.6359 ± 0.0330* | 17.62% |
| | 8 | 0.5512 ± 0.0577** | 28.59% |
| | 16 | 0.4996 ± 0.0333** | 35.28% |
| | 32 | 0.3688 ± 0.0171** | 52.22% |
| | 64 | 0.2640 ± 0.0395** | 65.80% |
| | 128 | 0.1564 ± 0.0206** | 79.74% |
| | 256 | 0.0984 ± 0.0222** | 87.25% |
| Taxol | 5 | 0.1825 ± 0.0163** | 76.38% |
| control | — | 0.7719 ± 0.0188 | 0.00% |

*P < 0.05
**P < 0.01 vs control.

The results showed that fusion protein I and protein II could significantly inhibit human glioma U87, and the inhibition rate reached 50% or more at a concentration of 32 μg/mL.

TABLE 8

Inhibitory effect of protein I and protein II on proliferation of cervical cancer cell Hela

| Group (n = 5) | Dose (μg/mL) | A570 nm/A630 nm | PI (%) |
|---|---|---|---|
| Protein I | 1 | 1.1729 ± 0.0183 | 8.28% |
| | 2 | 1.0658 ± 0.0295 | 16.66% |
| | 4 | 0.9739 ± 0.0238* | 23.84% |
| | 8 | 0.9526 ± 0.0166* | 25.51% |
| | 16 | 0.8248 ± 0.0105* | 35.50% |
| | 32 | 0.7109 ± 0.0119** | 44.41% |
| | 64 | 0.5643 ± 0.0265** | 55.87% |
| | 128 | 0.3629 ± 0.0215** | 71.62% |
| | 256 | 0.1461 ± 0.0350** | 88.58% |
| Protein II | 1 | 1.1066 ± 0.0282 | 13.47% |
| | 2 | 1.0001 ± 0.0162 | 21.72% |
| | 4 | 0.9368 ± 0.0835* | 26.74% |
| | 8 | 0.9812 ± 0.0179 | 23.27% |
| | 16 | 0.8276 ± 0.0395* | 35.28% |
| | 32 | 0.7018 ± 0.0133** | 45.12% |
| | 64 | 0.5845 ± 0.0499** | 54.29% |
| | 128 | 0.3792 ± 0.0213** | 70.35% |
| | 256 | 0.1456 ± 0.0845** | 88.61% |
| Taxol | 5 | 0.2078 ± 0.0162** | 83.75% |
| control | — | 1.2788 ± 0.0987 | 0.00% |

*P < 0.05
**P < 0.01 vs control.

The results showed that fusion protein I and protein II could significantly inhibit cervical cancer cell Hela, and the inhibition rate reached about 55% at a concentration of 64 μg/mL.

Taken together, the inhibitory effects of fusion protein I and protein II integrin blockers on proliferation of various tumor cells are shown in Tables 1-8. The fusion proteins can effectively inhibit proliferation of gastric cancer, lung cancer, liver cancer, breast cancer, melanoma, colon cancer, glioma, and cervical cancer. Among them, the inhibition rate of melanoma, gastric cancer and human glioma reached 50% or more at a concentration of 32 μg/mL; the inhibition rate of colon cancer cells reached 40% or more, and the inhibition rate of cervical cancer cells reached 50% or more at a concentration of 64 μg/mL; higher concentrations were required to achieve effective inhibition on lung cancer, liver cancer, and breast cancer cells.

Example 3

Detection of Inhibitory Effect of Fusion Proteins I and II on Migration of Human Umbilical Vein Endothelial Cells by Three-Dimensional Transwell Assay Human umbilical vein endothelial cells (HUVECs) were cultured with endothelial cell culture fluid containing 5% fetal bovine serum and 1×ECGS in a 5% $CO_2$ incubator at 37° C., to a confluence of 90% or more, and then inhibitory effect of fusion protein I and protein II on migration of endothelial cells were detected by transwell assay, in which only endothelial cells HUVEC of passage 2 to 8 were used, and the specific operation was as follows.

(1) 10 mg/mL Matrigel (a basement membrane matrix secreted by Engelbreth-Holm-Swarm (EHS) mouse sarcoma cells) diluted with a DMEM medium (Dulbecco's Modified Eagle Medium) at a ratio of 1:4, coated on a transwell chamber membrane, and air-dried at room temperature;

(2) HUVEC cells cultured to logarithmic phase were digested with 0.2% EDTA, collected, washed twice with PBS, followed by resuspended in an endothelial cell culture liquid containing 0.1% BSA, and counted under a microscope, and the cell concentration was adjusted to $1 \times 10^5$ cells/mL;

(3) Test solutions for each group were formulated and diluted to 100 μL with a cell culture liquid containing 0.1% BSA;

Groups were divided as follows:

Blank control group: a cell culture liquid containing no drug;

Endostar group: 5 mg/mL Endostar solution diluted to a predetermined concentration with a cell culture liquid containing no drug;

Fusion protein group: the fusion protein diluted to 10 μg/mL with a cell culture liquid containing no drug;

(4) The cells were inoculated into a transwell chamber, 100 μL per well, and test solutions for each group were added to the chamber. To a 24-well plate, 0.6 mL of endothelial cell culture liquid containing 5% fetal bovine serum and 1×ECGS was added to stimulate cell migration, and incubated at 5% $CO_2$ at 37° C. for 24 h;

(5) The culture liquid in the well was discarded. The cells were fixed with 90% alcohol at room temperature for 30 min, stained with 0.1% crystal violet for 10 min at room temperature, and rinsed with water. Un-migrated cells in the upper layer were gently wiped off by a cotton swab. The observation was carried out under a microscope and four fields of view were selected for taking photos and counting. The migration inhibition (MI) was calculated according to the formula:

$$MI(\%) = 1 - \frac{N_{test}}{N_{control}} \times 100\%$$

where $N_{test}$ is the migration cell number in the test group, and $N_{control}$ is the migration cell number in the blank control group.

Data Statistics:

The test was repeated 3 times independently. The results obtained from the test were calculated as mean±SD, and statistical t-test was performed. P<0.05 was considered as a significant difference, and P<0.01 was considered as extremely significant difference. The experimental results are shown in Table 9.

TABLE 9

Migration inhibition of HUVEC by protein I and protein II

| Group (n = 5) | Dose (μg/mL) | Migration cell number | MI (%) |
|---|---|---|---|
| Protein I | 0.25 | 2040.0 ± 180.21 | 18.17% |
| | 0.5 | 1738 ± 366.83* | 30.28% |
| | 1 | 933.0 ± 150.58** | 62.58% |
| | 2 | 731.0 ± 236.53** | 70.68% |
| | 4 | 786.0 ± 45.50** | 68.47% |
| | 8 | 1385.0 ± 176.11* | 44.44% |
| Protein II | 0.25 | 2122.0 ± 75.18 | 14.88% |
| | 0.5 | 1215.0 ± 221.60** | 51.26% |
| | 1 | 684.0 ± 28.58** | 72.56% |
| | 2 | 578.0 ± 275.42** | 76.82% |
| | 4 | 874.0 ± 141.50** | 64.94% |
| | 8 | 1758.0 ± 180.03* | 29.48% |
| Sunitinib | $8.0 \cdot 10^{-6}$ | 441.0 ± 150.58** | 82.31% |
| control | — | 2493.0 ± 85.12 | |

*P < 0.05
**P < 0.01 vs control.

It can be seen from the experimental results that under the action of fusion proteins I and II, the number of migrated endothelial cells was significantly reduced compared with that of the negative control, and the migration inhibition of HUVEC was significant at a concentration of 2 μg/mL. The inhibition rate was 70% or more, and the inhibition rate on cell migration was extremely significant compared with that of the negative control (P<0.01). Between 0.5 μg/mL and 4 μg/mL, the best inhibitory effect was achieved.

Example 4

Effect of Fusion Proteins I and II on Proliferation of Mouse Spleen Lymphocytes

The spleen of a mouse was taken out under sterile conditions, washed 3 times with an empty 1640 medium, ground in 5 mL syringe core, filtered through a 200-mesh sieve, and prepared into a single cell suspension, the single cell suspension was centrifuged (1000 rpm, 5 min), and the supernatant was discarded. Tris-NH$_4$Cl was used to break the red blood cells, which were allowed to stand in an ice water bath for 4 min and centrifuged (1000 rpm, 5 min), the supernatant was discarded, and the cells were washed twice with sterile PBS. Finally, cells were suspended in a 10% fetal calf serum RPMI 1640 culture liquid (5 mL), counted, adjusted to a cell concentration of 5×10$^6$ cells/mL, and cultured in a 96-well culture plate.

The experiment comprises a blank control group, a concanavalin A (ConA) group, a dexamethasone (Dex) group (0.02 mg/mL), and protein I and protein II used as experimental groups. After each group was added with spleen lymphocyte suspension, 100 μL per well, the blank control group was added with 100 μL of empty 1640 culture liquid, ConA group was added with ConA (final concentration of 5 μg/mL), and Dex group was added with Dex, and protein I and protein II were added with ConA (final concentration of 5 μg/mL) on the basis of addition of different concentrations of extracts. The cells were statically cultured in a cell incubator at 37° C. for 48 h. After the completion of the culture, 20 μL of MTT was added to each well, and the culture was continued for 4 h. Finally, all the solutions in each well were discarded, 100 μL of DMSO was added to each well, and the mixture was shaken and detected by a microplate reader for OD value at 570 nm. 5 parallels were preformed for per well. The experimental results are shown in Table 10.

TABLE 10

Effect of protein I and protein II on the proliferation of mouse spleen lymphocytes

| Group (n = 5) | Dose (μg/mL) | A570 nm/A630 nm | PI (%) |
|---|---|---|---|
| Protein I | 8 | 0.5520 ± 0.0182 | 6.27% |
| | 32 | 0.4902 ± 0.0122* | 16.76% |
| | 128 | 0.3741 ± 0.0911** | 36.47% |
| Protein II | 8 | 0.5633 ± 0.0237 | 4.35% |
| | 32 | 0.4963 ± 0.0886* | 15.72% |
| | 128 | 0.3965 ± 0.0122** | 32.67% |
| ConA | — | 0.6201 ± 0.0349 | — |
| Dex | 20 | 0.3468 ± 0.1144** | 41.11% |
| control | — | 0.5889 ± 0.0528 | |

*P < 0.05
**P < 0.01 vs control.

The results showed that fusion protein I and protein II could inhibit mouse spleen lymphocytes to some extent compared with the ConA group.

Example 5

Effect of Fusion Proteins I and II on IL-1β Production by Mouse Peritoneal Macrophages (1) IL-1β production: mice were intraperitoneally injected with 1 mL of broth medium containing 6% starch, and three days later, the mouse peritoneal macrophages were aseptically taken, washed twice with a 1640 medium, adjusted to the cell concentration of 2×10$^6$ cells/mL, inoculated into a 24-well culture plate, 1 mL/well, incubated for 3 h in a cell culture incubator, and shaken once every 30 min, so that the cells were allowed to adhere sufficiently. Then, the cells were washed twice with a culture liquid to remove unadhered cells. The blank group was added with PBS, the positive group was added with the positive drug dexamethasone Dex, and the control groups were the low, medium and high concentrations of fusion protein I and protein II. After administration, the culture was continued for 48 h, the cells were centrifuged at 1000 r/min for 15 min. The supernatant was taken as a sample for testing activity of IL-1β.

(2) Determination of IL-1β content: the detection was performed by using mouse IL-1β enzyme-linked immunosorbent assay kit from R&D company. According to the instructions of the kit, the procedures were as follows: the reaction well for the test samples and standards with different concentration were sealed with sealing tapes, respectively, incubation was performed at 37° C. for 90 min; the plate was washed four times; a biotinylated antibody working solution (100 μL/well) was added, the reaction well was sealed with sealing tapes, and incubation was performed at 37° C. for 60 min; the plate was washed four times; an enzyme conjugate working solution (100 μL/well) was added, the reaction well was sealed with sealing tapes, incubation was performed at 37° C. for 30 min; the plate was washed four times; a developer (100 μL/well) was added, incubation was performed at 37° C. away from light for 10 to 20 min, a stop solution (100 μL/well) was added and mixed, and the OD450 value was measured. The experimental results are shown in Table 11.

TABLE 11

Effect of protein I and II on IL-β production by mouse peritoneal macrophages

| Group (n = 5) | Dose (μg/mL) | IL-1β (pg/ml) | PI (%) |
|---|---|---|---|
| Protein I | 8 | 722.85 ± 9.95 | 16.04% |
|  | 32 | 495.30 ± 14.58* | 42.47% |
|  | 128 | 322.56 ± 13.52** | 62.53% |
| Protein II | 8 | 755.56 ± 17.82 | 12.24% |
|  | 32 | 610.06 ± 19.97* | 29.14% |
|  | 128 | 468.96 ± 12.59** | 45.53% |
| Model group | 20 | 860.96 ± 5.53* |  |
| Dex | 20 | 322.46 ± 20.56** | 61.38% |
| control | — | 8.79 ± 2.26* |  |

*$P < 0.05$,
**$P < 0.01$ vs control.

The results showed that fusion protein I and II could significantly inhibit IL-1β production by mouse peritoneal macrophages.

Example 6

Effect of Fusion Proteins I and II on Subacute Inflammation of Tampon Granuloma in Rat 40 parts of degreasing cotton, 30 mg for each part, were accurately weighed with an analytical balance and kneaded into balls having substantially the same shape and size, which were autoclaved at 1.5 kpa for 30 min and dried at 50° C. for further use.

40 male SD rats were randomly divided into 4 groups with 10 rats for each group. The groups were a model group, a dexamethasone positive group (10 mg/kg), and fusion protein I and protein II experimental groups at an effective dose of 64 mg/kg, respectively. Rats were anesthetized with sodium pentobarbital (40 mg/kg) via intraperitoneal injection before administration. The abdominal coat was cut off, and the skin of the middle of the lower abdomen was cut under sterile conditions. The incision was about 1 cm long and the subcutaneous tissue was expanded with a vascular clamp. A sterile dry tampon was subcutaneously implanted into one side of the groin, the incision was sutured, and an appropriate amount of amoxicillin was spread at the incision to prevent infection. After the surgery is finished, the groups were administered once by injection every 5 days from the day of surgery. On day 7, the rats were sacrificed by cervical dislocation at the 24th hour after administration, the inguinal skin was cut, the tampon was taken out together with the surrounding granulation tissue and the surrounding tissue was removed. After drying for additional 48 h in an oven at 60° C., the weight was accurately weighed. The granuloma weight was calculated: granuloma weight (mg/100 g body weight)=net weight of granulation (mg)/rat body weight (100 g). The experimental results are shown in Table 12.

TABLE 12

Effect of protein I and protein II on subacute inflammation of tampon granuloma in rat

| Group (n = 10) | Weight gain (g) | Granuloma (mg)/Weight (100 g) | PI (%) |
|---|---|---|---|
| Protein I (64 mg/kg) | 32.09 ± 10.55* | 0.37 ± 0.09* | 19.57% |
| Protein II (64 mg/kg) | 33.89 ± 9.79** | 0.38 ± 0.02** | 17.39% |
| Dex (10 mg/kg) | −32.98 ± 7.68** | 0.22 ± 0.06** | 52.17% |
| control | 26.62 ± 5.59* | 0.46 ± 0.12* |  |

*$P < 0.05$,
**$P < 0.01$ vs control.

The experimental results showed that fusion protein I and II could significantly inhibit tampon granuloma in rat at an effective dose of 64 mg/kg, compared with the blank model group. Although the positive drug had a higher inhibition rate, the weight loss of the rat was obvious, and the side effects were larger. In contrast, the fusion protein was relatively safe.

Example 7

Effect of Fusion Proteins I and II on Peritoneal Capillary Permeability in Mice

80 Kunming mice were randomly divided into 8 groups with 10 mice for each group, which were a blank model group, a dexamethasone positive group (10 mg/kg), and fusion protein I, protein II experimental groups at high, medium and low doses (128, 32, 8 mg/kg), respectively. The drug was administered once by injection every 5 days, and the blank model group was given an equal volume of physiological saline for 5 days and fed normally. On the 5th day after the administration, a 5 g/L of Evans blue physiological saline solution was injected into the tail vein at 10 kg/mL, followed by intraperitoneal injection (10 kg/mL) HAc solution (6 mL/L) to induce inflammation. After 20 min, the mice were sacrificed by cervical dislocation. 5 mL of physiological saline was intraperitoneally injected, the abdomen was gently rubbed for 2 min, the abdominal cavity was cut, a peritoneal washing solution was collected and centrifuged at 4000 rpm for 10 min, 1 mL of supernatant was taken, and 3 mL of physiological saline was added to obtain a 4 mL of dilution. The absorbance OD value of the dilution was measured by an ultraviolet spectrophotometer at a wavelength of 590 nm, and the amount of pigment exudation was expressed by the OD590 nm value, and peritoneal capillary permeability in mice was examined. The experimental results are shown in Table 13.

TABLE 13

Effect of protein I and protein II on peritoneal capillary permeability in mice

| Group (n = 10) | Dose (mg/kg) | Exudation rate (OD590) | PI (%) |
|---|---|---|---|
| Protein I | 8 | 0.59 ± 0.02 | 10.61% |
|  | 32 | 0.46 ± 0.02* | 30.30% |
|  | 128 | 0.35 ± 0.05** | 46.97% |
| Protein II | 8 | 0.55 ± 0.07 | 16.67% |
|  | 32 | 0.42 ± 0.09* | 36.36% |
|  | 128 | 0.31 ± 0.06** | 53.03% |
| Dex | 10 | 0.27 ± 0.03** | 59.09% |
| control | — | 0.66 ± 0.04* |  |

*$P < 0.05$,
**$P < 0.01$ vs control.

The results showed that fusion protein I and II could significantly inhibit the increase of peritoneal capillary permeability in mice induced by glacial acetic acid. The higher the dose, the stronger the effect.

Example 8

Effect of Fusion Proteins I and II on Xylene-Induced Ear Swelling in Mice

80 Kunming mice were divided into 8 groups with 10 mice for each group and numbered. A physiological saline group was used as a blank control group, an aspirin group (200 mg/kg) was used as a positive control group, and fusion proteins I and II at high, medium and low doses (128, 32, 8 mg/kg) was used as the experimental groups. Mice were administered once by injection every 5 days. The blank control group was given an equal volume of physiological saline. On the fifth day after the administration, 0.05 mL of xylene was applied to both sides of the right ears of the mice to induce inflammation, and the left ears were not applied and were normal ears. After 2 h, the mice were sacrificed by dislocation, and the ears were cut along the auricle. Ear pieces were taken with a puncher and weighed, and the swelling degree and swelling rate were calculated. Swelling degree=right ear piece weight-left ear piece weight, swelling rate=(swelling degree/left ear piece weight)×100%. The experimental results are shown in Table 14.

TABLE 14

Effect of protein I and protein II on xylene-induced ear swelling in mice

| Group (n = 10) | Dose (mg/kg) | Swelling degree (mg) | PI (%) |
| --- | --- | --- | --- |
| Protein I | 8 | 6.18 ± 0.20 | 7.21% |
|  | 32 | 5.21 ± 0.31* | 21.77% |
|  | 128 | 4.19 ± 0.28** | 37.09% |
| Protein II | 8 | 5.92 ± 0.15 | 11.11% |
|  | 32 | 5.01 ± 0.84* | 24.77% |
|  | 128 | 3.89 ± 0.39** | 41.59% |
| Aspirin | 200 | 3.12 ± 0.61** | 53.15% |
| control | — | 6.56 ± 0.47* |  |

*$P < 0.05$,
**$P < 0.01$ vs control.

The experimental results showed that high doses of fusion proteins I and II could significantly inhibit xylene-induced ear swelling in mice, and the inhibitory effect could be enhanced with the increase of dose.

Example 9

Effect of Fusion Proteins I and II on Acute Inflammation of Toe Swelling in Rat Induced by Carrageenan 80 SD rats were randomly divided into 8 groups with 10 mice for each group. The groups were a blank model group, a dexamethasone positive group (5 mg/kg) and fusion protein I and protein II experimental groups at high, medium and low doses (128, 32, 8 mg/kg), respectively. The drug was administered once by injection every 5 days, and the model group was given an equal volume of physiological saline for 3 days and fed normally. On the third day after the administration, 0.1 mL of 1% carrageenan was injected subcutaneously into the right hind toes of the rats to induce inflammation. The foot volume was measured at 1 h, 3 h, 5 h, and 7 h after inflammation. The swelling degree of the foot was calculated according to the following formula: the swelling degree of the foot (mL)=the volume of the foot after inflammation–the volume before inflammation. The number of milliliters of spilled liquid was recorded (method: the protruding point of the right joint was circled with a ballpoint pen and used as a measurement mark, and the right hind feet of the rats were sequentially placed in the volume measuring device, so that the hind limbs were exposed outside the cylinder, and the depth of the immersion was limited to the overlap of the circle and the liquid level. After the foot entered the liquid, the liquid level was raised, and the volume of the spilled liquid was the volume of the right hind foot of the rat, and the normal volume of the right hind foot of each mouse is sequentially determined). The experimental results are shown in Table 15.

TABLE 15

Effect of protein I and protein II on acute inflammation of toe swelling in rat induced by carrageenan

| Group (n = 10) | Dose (mg/kg) | Swelling degree(mL) | | | |
| --- | --- | --- | --- | --- | --- |
| | | 1 h | 3 h | 5 h | 7 h |
| Protein I | 8 | 0.27 ± 0.13 | 0.41 ± 0.15 | 0.44 ± 0.15 | 0.35 ± 0.09* |
|  | 32 | 0.29 ± 0.07* | 0.36 ± 0.21 | 0.37 ± 0.14* | 0.34 ± 0.11* |
|  | 128 | 0.28 ± 0.15* | 0.32 ± 0.08** | 0.34 ± 0.21* | 0.32 ± 0.18** |
| Protein II | 8 | 0.26 ± 0.13 | 0.42 ± 0.12* | 0.42 ± 0.13 | 0.38 ± 0.08* |
|  | 32 | 0.25 ± 0.21 | 0.30 ± 0.14* | 0.35 ± 0.09* | 0.32 ± 0.19 |
|  | 128 | 0.27 ± 0.05* | 0.32 ± 0.15* | 0.33 ± 0.10** | 0.31 ± 0.16** |
| Dex | 10 | 0.21 ± 0.11** | 0.26 ± 0.10** | 0.26 ± 0.11** | 0.25 ± 0.09* |
| control | — | 0.26 ± 0.22 | 0.44 ± 0.17 | 0.54 ± 0.06 | 0.39 ± 0.21 |

*$P < 0.05$,
**$P < 0.01$ vs control.

The experimental results showed that the toes of the rats in each group were rapidly swollen after modeling, and the peak of swelling was reached at about 3-5 h, which began to subside at 7 h. The fusion proteins I and II at high dose could significantly inhibit toe swelling in rat induced by carrageenan, and the inhibitory effect was not significant at low dose.

Example 10

Effect of Fusion Proteins I and II on Chronic Inflammation of Adjuvant Arthritis in Rat Model Establishment:

80 SPF SD rats were randomly divided into 8 groups. Rats in each group were lightly anesthetized with ether. Then, 0.1 mL of complete Freund's adjuvant containing inactivated *Mycobacterium tuberculosis* was injected subcutaneously into the left hind foot of the rats. Primary arthritis occurred in the left hind foot of the rat, and at about 13 days post-modeling, secondary arthritis occurred in the right hind foot. A blank control group was injected with an equal volume of physiological saline. The drug was administered 13 days after modeling. The methotrexate group was administered once by injection every 5 days for 15 days, 4 times in total; the fusion protein I and protein II at high, medium and low doses (128 mg/kg, 32 mg/kg, 8 mg/kg) were administered by injection once every 5 days for 15 days.

Efficacy Evaluation:

1. Primary and Secondary Toe Swelling Degree

Using a foot volume measuring method, a marker was made with a fat-soluble marker at the left and right posterior ankle joints of each rat, and the left and right hind feet of the animal were respectively immersed in the volume measuring device. The immersion depth was bounded by the marker, and the reading value at the scale pipette of the device was the initial volume of the animal's left and right hind feet.

The day of modeling was considered as the 0th day and recorded as d0. The volume of the left hind foot (modeling foot) was measured from the first day d1 after modeling every 2 days. When the swelling occurred (i.e., secondary arthritis occurred) at the contralateral non-inflammatory foot (right hind foot), the administration was started. The volume of the left and right hind feet was measured once every 2 days, and the degree of primary and secondary toe swelling was determined, which was calculated as follows:

Primary toe swelling (mL)=left hind foot volume on the day of measurement−initial volume of left hind foot Secondary toe swelling (mL)=right hind foot volume on the day of measurement−initial volume of right hind foot 2. Clinical Score Systemic score: the systemic score was taken every 2 days after the onset of secondary inflammation.

Hind foot: no swelling=0 score, one hind foot swelling=1 score, two hind feet swelling=2 scores;

Forefoot: no swelling=0 score, one forefoot swelling=1 score, two forefeet swelling=2 scores;

Ears: no redness and nodules=0 score, redness or nodules in one ear=1 score, redness and nodules in both ears=2 scores;

Nose: no swelling=0 score, obvious swelling=1 score;

Tail: no nodules=0 score, nodules=1 score; full score was 8 scores.

Arthritis index score: the arthritis index score was performed every 2 days after the onset of secondary inflammation.

Normal=0 score; erythema and mild swelling in the ankle joint=1 score; erythema and mild swelling from the ankle to the metatarsophalangeal joint or metacarpal joint=2 scores; erythema and moderate swelling from the ankle to the metatarsophalangeal joint or metacarpal joint=3 scores; erythema and severe swelling from the ankle to the metatarsophalangeal joint or metacarpal joint=4 scores; each foot had a full score of 4 scores, and each rat had a maximum score of 16 scores.

3. Weight Gain

The initial body weight of each group of rats was weighed before modeling. The body weight was measured every 2 days from d1 after modeling, from which the initial body weight was subtracted to obtain the weight gain of each group of rats. The experimental results are shown in Table 16.

TABLE 16

Effect of protein I and protein II on chronic inflammation of adjuvant arthritis in rat

| Group (n = 10) | Dose (mg/kg) | Foot swelling degree (mL) | | | Clinical score | Weight gain (g) |
|---|---|---|---|---|---|---|
| | | Left | Right | Whole body | Arthritis index | |
| Protein I | 8 | 1.94 ± 0.31 | 1.97 ± 0.08 | 2.09 ± 0.17* | 6.79 ± 0.52 | 44.14 ± 21.57 |
| | 32 | 1.67 ± 0.04** | 1.56 ± 0.22* | 1.84 ± 0.43 | 5.75 ± 0.47* | 48.61 ± 16.92* |
| | 128 | 1.41 ± 0.17** | 1.35 ± 0.08** | 1.54 ± 0.08** | 4.36 ± 0.45** | 51.87 ± 16.34* |
| Protein II | 8 | 1.88 ± 0.08 | 1.89 ± 0.55 | 2.14 ± 0.25* | 6.97 ± 0.57 | 45.29 ± 11.82 |
| | 32 | 1.59 ± 0.23* | 1.63 ± 0.33* | 1.89 ± 0.37 | 5.68 ± 0.44* | 47.91 ± 19.30* |
| | 128 | 1.35 ± 0.17** | 1.37 ± 0.77* | 1.57 ± 0.18** | 4.23 ± 0.69** | 50.88 ± 15.37** |
| Methotrexate | 1 | 1.22 ± 0.21** | 1.25 ± 0.13** | 1.34 ± 0.19** | 2.96 ± 0.57** | 47.35 ± 17.40** |
| control | — | 2.14 ± 0.09 | 2.12 ± 0.18 | 2.59 ± 0.28 | 7.54 ± 0.36 | 29.50 ± 20.32 |

*$P < 0.05$,
**$P < 0.01$ vs control.

The experimental results showed that after modeling, the left hind foot in each group was swollen rapidly (primary inflammation), and on the 13th day, the hind foot (non-contralateral inflammatory foot) began to be red and swollen (i.e., secondary inflammation occurred). The arthritis index and systemic score began to increase, reaching the highest value on the 19th day, and the swelling degree and score of each group were gradually decreased along with administration. The primary toe swelling degree was used to reflect the therapeutic effect of each treatment group on primary arthritis. The high and medium doses of each administration group could treat primary arthritis to a certain extent compared with the model group. The positive drug methotrexate had the best effect, and the fusion protein I and protein II were effective in high dose groups, with extremely significant differences (**P<0.01). The secondary toe swelling degree was used to reflect the therapeutic effect of each treatment group on secondary arthritis.

Example 11

Inhibitory Effect of Fusion Proteins I and II on Proliferation of Human Retinal Vascular Endothelial Cell (HRCEC)

The activity of the integrin blocker polypeptide to inhibit proliferation of human retinal vascular endothelial cells was examined by MTT assay. HRCEC cells were cultured in a 5% $CO_2$ incubator at 37° C. to a density of 90% or more, and then collected by trypsinization. The cells were resuspended in the culture liquid and counted under a microscope. The cell concentration was adjusted to $3.0 \times 10^4$ cells/mL. The cell suspension was inoculated into a 96-well plate, 100 μL per well, and cultured overnight in a 5% $CO_2$ incubator at 37° C. The polypeptide I, the polypeptide II, the polypeptide III, and the Avastin® (bevacizumab) were diluted with the culture liquid to respective predetermined concentrations. After the cells were fully adhered, each dilution was added to a 96-well plate, 100 μL per well, respectively. The integrin blocker polypeptide was used as an administration group, and Avastin® (bevacizumab) was used as a positive control group, and a culture liquid containing no drug was used as a blank control group, which were incubated in a 5% $CO_2$ incubator at 37° C. for 48 hours. 20 μL of 5 mg/mL MTT was added to each well of a 96-well plate, and incubation was continued for 4 hours. The medium was aspirated and 100 μL of DMSO was added per well for dissolution. The absorbance was measured at 570 nm with a microplate reader with a reference wavelength of 630 nm, and the proliferation inhibition (PI) was calculated. The formula was as follows:

$$PI(\%) = 1 - \frac{N_{test}}{N_{control}} \times 100\%$$

where $N_{test}$ is the OD value of the test group and $N_{control}$ is the OD value of the blank control group.

Data Statistics:

The test was repeated 5 times independently. The results obtained from the test were calculated as mean±SD, and statistical t-test was performed. P<0.05 was considered as a significant difference, and P<0.01 was considered as an extremely significant difference. The experimental results are shown in Table 17.

TABLE 17

Inhibitory effect of protein I and protein II on proliferation of human retinal vascular endothelial cell (HRCEC)

| Group (n = 5) | Dose (μg/mL) | A570 nm/A630 nm | PI (%) |
|---|---|---|---|
| Protein I | 1 | 1.0639 ± 0.0162 | 12.94% |
| | 2 | 1.0025 ± 0.0329 | 17.96% |
| | 4 | 1.0750 ± 0.0324* | 12.03% |
| | 8 | 0.9567 ± 0.0467* | 21.71% |
| | 16 | 0.8459 ± 0.0731* | 30.78% |
| | 32 | 0.7126 ± 0.0486** | 41.69% |
| | 64 | 0.5618 ± 0.0222** | 54.03% |
| | 128 | 0.4567 ± 0.0181** | 62.63% |
| | 256 | 0.3274 ± 0.01.6** | 73.21% |

TABLE 17-continued

Inhibitory effect of protein I and protein II on proliferation of human retinal vascular endothelial cell (HRCEC)

| Group (n = 5) | Dose (μg/mL) | A570 nm/A630 nm | PI (%) |
|---|---|---|---|
| Protein II | 1 | 1.0588 ± 0.0247 | 13.36% |
| | 2 | 1.0079 ± 0.0392 | 17.52% |
| | 4 | 1.0380 ± 0.0712* | 5.06% |
| | 8 | 0.9911 ± 0.0697 | 18.90% |
| | 16 | 0.8865 ± 0.0143* | 27.45% |
| | 32 | 0.7142 ± 0.0199** | 41.55% |
| | 64 | 0.5911 ± 0.0478** | 51.63% |
| | 128 | 0.4632 ± 0.0597** | 62.09% |
| | 256 | 0.3354 ± 0.0858** | 72.55% |
| Avastin ® (bevacizumab) control | 5 | 0.4544 ± 0.0288** | 62.82% |
| | — | 1.2222 ± 0.0464 | 0.00% |

*P < 0.05,
**P < 0.01 vs control.

The results showed that fusion proteins I and II could significantly inhibit the proliferation inhibition of human retinal vascular endothelial cells (HRCECs) in a dose-dependent manner. At a concentration of 64 μg/mL, the inhibition rate reached 50% or more.

Example 12

Activity of Fusion Proteins I and II to Inhibit Angiogenesis In Vivo Analyzed by Chicken Embryo Chorioallantoic Membrane (CAM)

In this study, CAM assay was used to investigate the activity of fusion protein I and protein II to inhibit angiogenesis in vivo. The study has shown that the biosynthesis rate of collagen reached the maximum on the 8th to 11th day of chicken embryo development, which was the most vigorous stage of angiogenesis, and the body's immune system had not yet been fully established at that time, and thus the chicken embryos developed to the 8th day was selected to be administered. Considering that the polypeptide on drug-loaded paper had a certain diffusion range limitation on the chicken embryo chorioallantoic membrane, only the number of new blood vessels within a radius of 5 mm from the edge of the paper was counted in the test. The following steps were used:

(1) The White Leghorn chicken embryos on day 6 were cultured in a 37° C. incubator at 60%-70% humidity for two days.

(2) A 1.0 cm×1.0 cm window was drilled above the chicken embryo air sac, and the inner membrane was torn off with forceps to expose the chorioallantoic membrane. Lens paper having a diameter of 5 mm was used as a loading carrier, and was placed on the chorioallantoic membrane of the chicken embryo air sac. Filter paper with PBS was used as a blank group, and an administration group was added with different doses of fusion protein. The positive control was Avastin® (bevacizumab).

(3) The chicken embryo air sac was sealed with a sterile transparent tape, and after culturing at 37° C. for 72 hours, the chicken embryo air sac was opened, and a fixative (formaldehyde:acetone=1:1) was added for fixation for 15 minutes. The chorioallantoic membrane to which the lens paper was adhered was taken out, the distribution of the new blood vessels was observed, and the new blood vessels were counted and photographed. Five replicates were set for each dose and the results were statistically analyzed.

The analysis results of the activity of fusion protein to inhibit angiogenesis in vivo by the chicken embryo chorioallantoic membrane (CAM) assay were as follows: negative control was treated with PBS, the dose of positive control Avastin® (bevacizumab) was 10 fusion protein I and protein II was used to treat the chicken embryos at high, medium and low doses of 128 µg, 32 µg and 8 µg, respectively. The results are shown in Table 18.

TABLE 18

Inhibitory effect of protein I and protein II on angiogenesis of chicken embryo chorioallantoic membrane

| Group (n = 5) | Dose (µg) | Blood vessel number | PI (%) |
| --- | --- | --- | --- |
| Protein I | 8 | 89 ± 8 | 32.58% |
|  | 32 | 81 ± 3 | 38.64% |
|  | 128 | 55 ± 10** | 58.33% |
| Protein II | 8 | 105 ± 12 | 20.45% |
|  | 32 | 86 ± 13 | 34.85% |
|  | 128 | 69 ± 8* | 47.73% |
| Avastin ® (bevacizumab) | 10 | 63 ± 17** | 52.27% |
| control | — | 132 ± 15 | 0.00% |

*$P < 0.05$,
**$P > 0.01$ vs control.

The results showed that fusion protein I and protein II could inhibit angiogenesis in CAM, and had a strong inhibitory effect (nearly 50%) at high dose.

Example 13

Effect of Fusion Proteins I and II on Corneal Neovascularization in Mice (1) Preparation of Corneal Neovascularization Model Induced by Alkali Burn in BALB/c Mice:

15 healthy male BALB/c mice with weight of 20-25 g were examined under a slit lamp microscope for the anterior segment of both eyes and the appendage to exclude ocular lesions. The eyes were given 0.3% loxacin eye drops 1 day before the preparation of alkali burn model, twice a day. After the mice were anesthetized by intraperitoneal injection of 1.8% Avertin, single-layer filter paper with a diameter of 2 mm was clamped with tweezers, and immersed in a 1 mol/L sodium hydroxide solution to reach a saturated state, and the excess liquid was removed. The filter paper was placed in the central corneal of BALB/c mice for 40 s and then discarded, and the burned area and conjunctival sac were immediately rinsed with 1 mL of PBS for 1 min. Excess water was wiped away with cotton swabs, and under an operating microscope, the corneal epithelium was vortically scraped off by paralleling a corneal scraping knife to the limbus corneae. The subcutaneous stromal layer and limbus corneae was carefully not to be injured, and after surgery, an erythromycin eye ointment was applied into the conjunctival sac to prevent infection.

(2) Experimental Animal Grouping and Sample Acquisition:

15 mice were randomly divided into fusion protein I and protein II groups and a control group, with 5 rats in each group. After alkali burn, 64 µg of fusion protein I and 64 µg of protein II and saline were given once via intravitreal injection every 7 days, and the inflammatory reaction and neovascularization of the cornea in each group were observed under a slit lamp microscope on day 1, day 7, and day 14 after alkali burn. On day 14 after alkali burn, the corneal neovascularization in each group was photographed and recorded under the slit lamp microscope for photographing anterior segment of the eye. Then, all the mice were sacrificed by cervical dislocation and the eyeballs were removed. The blood was washed with physiological saline, and the eyeballs were fixed in 4% paraformaldehyde for 1.5 h, dehydrated in PBS containing 30% sucrose overnight, embedded in an OCT tissue freezing medium, stored in a refrigerator at −80° C., subjected to cryosection at 8 µm, and detected by immunohistochemistry for CD31 expression.

(3) Quantitative Measurement for Microvessel Density of Corneal Tissue:

Microvessel density (MVD) is an indicator for evaluating angiogenesis. An anti-CD31 antibody immunohistochemistry was used to label vascular endothelial cells and the number of microvessels per unit area was counted to measure the extent of neovascularization. Standards for counting microvessels were that under a microscope, the endothelial cells or cell clusters which were clearly demarcated from adjacent tissues in the corneal tissue and were stained tan or brown were counted as the new blood vessels. The number of new blood vessels in the entire section was counted under a 10×20 microscope. After the corneal tissue was photographed, the area of the entire corneal tissue was calculated by image processing software Image J, and the density of new blood vessels in the entire section in this example was determined. The results are shown in Table 19.

TABLE 19

MVD count showing effect of protein I and protein II on corneal neovascularization in mice

| Group (n = 5) | Dose (µg) | MVD |
| --- | --- | --- |
| Protein I | 64 | 27.38 ± 6.13* |
| Protein II | 64 | 23.98 ± 4.50* |
| control | — | 52.11 ± 7.85* |

*$P < 0.05$,
**$P < 0.01$ vs control.

The results showed that CD31 was used as a microvascular marker, which was mainly expressed in the cytoplasm of vascular endothelial cells. The stained positive cells were vascular endothelial cells stained tan or brown without background staining. The number of CD31-positive new blood vessels in fusion protein I and II experimental groups was significantly reduced compared with that of the control group. Fusion protein I and II groups had significant difference compared with the control group. The experimental results showed that fusion protein I and II could inhibit the growth of corneal new blood vessels, and can be used as a drug for the treatment of corneal neovascular eye diseases.

Example 14

Effect of Fusion Proteins I and II on Iris Neovascularization in Rabbits

The argon ion laser at 577 nm was used to occlude the major branch vein of rabbit retina, and a success venous occlusion was confirmed by fundus fluorescein angiography (FFA). After 5-12 days, the iris fluorescein angiography (IFA) showed that the fluorescein leakage was obvious in the iris vessels compared with the normal control group, confirming the formation of the animal model of the iris neovascularization (NVI).

9 eyes successful in modeling were randomly divided into 3 groups with 3 eyes for each group. They were labeled as a negative control group, and fusion protein I and II treatment groups, respectively, which were respectively given physiological saline, 128 µg of fusion protein I and 128 µg of fusion protein II via intravitreal injection once every 7 days for 2 weeks. The observation was performed with an optical and electron microscope on the third week.

Results: under the optical microscope, it was observed that the anterior surface of the iris was a fibrous vascular membrane remnant mainly consisting of fibrous tissue, and there were few open vascular lumens. Vascular residues can be seen in the iris matrix, which are necrotic cells and cell debris. The iris surface of the control eye under a light microscope is a fibrous vascular membrane with branches and potential lumens.

The ultrastructure of the iris in the treatment group showed a series of degenerative changes. The endothelial cells of the large blood vessels in the middle of the iris matrix had normal nucleus, cytoplasm and cell junctions. There were capillary residues in the iris matrix and on the anterior surface of the iris, which were surrounded by cell debris and macrophage infiltration. No capillary with potential lumens and degenerated parietal cells indicated regression of new blood vessels.

Through animal model experiments of iris neovascularization, it was demonstrated that fusion protein I and fusion protein II could inhibit neovascularization and regress the formed blood vessels.

Example 15

Effect of Fusion Proteins I and II on Choroidal Blood Flow in Rabbit Eyes

New Zealand white rabbits with weight of 2.5-3.0 kg were randomly divided into 3 groups, which were labeled as a control group, and fusion protein I and II groups. White rabbits in each group were anesthetized with 35 mg/kg xylazine via intramuscular injection, and then anesthesia was maintained with half of the initial amount via intramuscular injection per hour. The intraocular pressure of the left eye was increased to 40 mmHg, under which the blood flow can be reduced to ⅓ of the normal value. The left ventricle was cannulated through right carotid artery for injection of microspheres (for the calculation of ocular blood flow), and the femoral artery was cannulated for blood collection. Each group was given physiological saline, 128 µg of fusion protein I and 128 µg of fusion protein II via intravitreal injection. The ocular blood flow of rabbit eyes with high intraocular pressure was measured by a color microsphere technique at 0, 30, and 60 minutes after administration. At each time point, 0.2 mL (about 2 million) of microspheres were injected. Immediately after the microspheres were injected, blood was collected through the femoral artery for 60 seconds, and placed in a heparinized anticoagulant tube, and the amount of blood collected was recorded. After the last blood collection, the animals were sacrificed with 100 mg/kg phenobarbital via intravenous infusion. The eyeballs were removed, and the retina, choroid, iris and ciliary body were separated, and the tissue weight was recorded. The tissue blood flow at each time point was calculated with the following formula: $Qm=(Cm \times Qr)/Cr$, where $Qm$ represented tissue blood flow in µL/min/mg; $Cm$ was the number of microspheres per milligram of tissue; $Qr$ was blood flow in µL/min; and $Cr$ was the number of blood microspheres as a reference. The experimental results are shown in Table 20.

TABLE 20

Effect of protein I and protein II on choroidal blood flow in white rabbit eyes

| Group (n = 3) | Dose (µg) | Time (mm) | Blood flow (µL/min/mg) |
|---|---|---|---|
| Protein I | 128 | 0 | 23.1 ± 2.6 |
| | 128 | 30 | 17.5 ± 3.1 |
| | 128 | 60 | 14.3 ± 1.9 |
| Protein II | 128 | 0 | 23.3 ± 2.7 |
| | 128 | 30 | 15.6 ± 1.2 |
| | 128 | 60 | 14.6 ± 1.4 |
| control | — | 0 | 12.7 ± 1.4 |
| | — | 30 | 9.6 ± 1.8 |
| | — | 60 | 5.8 ± 1.9 |

The results showed that choroidal blood flow was significantly increased in the fusion proteins I and II treatment groups at all observation time points.

Example 16

Effect of Fusion Proteins I and II on Retinal Blood Vessels in OIR Mice

Establishment of the OIR model: young mice and their mothers were exposed to 75% hyperoxic environment from day 7 to day 12 after birth of C57/B16 mice so that capillaries in the central retina rapidly disappeared. On day 12, the mice were returned to indoor air and the retinal blood vessels exposed to hyperoxia rapidly disappeared, which caused extensive abnormal neovascularization, and the central part of the retina remained largely avascular for a long time. After the blood vessels disappeared completely, the fusion protein (administration group, the doses of fusion proteins I and II were both 64 µg) or physiological saline (negative group) was injected into the vitreous body on day 13. Retinal vessels were evaluated on day 17 (labeled as unclosed vessels, 50 mL of Texas Red-labeled tomato lectin was injected into the left ventricle and cycled for 5 minutes). The experimental results are shown in Table 21.

TABLE 21

Effect of protein I and protein II on retinal blood vessels in OIR mice

| Group (n = 5) | Dose (µg) | Area (mm²) | Reduce (%) |
|---|---|---|---|
| Protein I | 64 | 0.111 ± 0.027* | 52.97% |
| Protein II | 64 | 0.153 ± 0.022* | 35.17% |
| control | — | 0.236 ± 0.039 | 0.00% |

*$P < 0.05$,
**$P < 0.01$ vs control.

The results showed that the administration of fusion proteins I and II to OIR mice could alleviate pathological neovascularization. Compared with the negative control, the neovascular clusters in the retina of OIR mice treated with fusion proteins I and II were significantly reduced, and the areas occupied by neovascular clusters were decreased by 52.97% and 35.17%, respectively.

Example 17

Effect of Fusion Proteins I and II on Neovascularization in Premature Rat Retinopathy Model A fluctuating oxygen-induced animal model was adopted, and newborn rats (within 12 hours) spontaneously delivered on the same day were randomly divided into three groups: an oxygen model group, an oxygen treatment group, and a normal control group. The oxygen model was subdivided into three model subgroups, which were placed in a semi-closed oxygen chamber made of plexiglass together with the treatment group. The medical oxygen was introduced into the chamber, and the oxygen concentration was adjusted to 80%±2% with an oxygen meter. After 24 hours, nitrogen gas was introduced into the oxygen chamber, and then the oxygen concentration was rapidly adjusted to 10%±2% and maintained for 24 hours. The operation was repeated, the oxygen concentration in the oxygen chamber was maintained to be alternated between 80% and 10% every 24 hours for 7 days, and then the rats were transferred to the air and fed. The oxygen concentration was monitored 8 times a day, and the ambient temperature in the chamber was controlled to 23° C.±2° C. The litter was replaced, food was added, water was changed, and mother rat was replaced once. The normal control group was placed in an animal house feeding environment. Compared with the control group, if the retinal stretched preparation stained with ADPase in the model group showed obvious vascular changes, the nucleus count of vascular endothelial cells that broke through the inner limiting membrane of the retina into the vitreous body was increased, and the difference was statistically significant, the model was successfully established.

The oxygen treatment group was divided into two subgroups. On day 7 of modeling, the administration was performed via intravitreal injection, in which the fusion proteins I and II were administered at a dose of 100 μg, respectively. The rats in the oxygen model group and the control group were given only physiological saline for one week.

On day 14, after the rats was sacrificed with ether anesthesia, the eyeballs were removed and fixed in a 40 g/L paraformaldehyde solution for 24 hours. The eyeballs were dehydrated with gradient alcohol and hyalinized with xylene. After being immersed in wax, the eyeballs were continuously sectioned to a thickness of 4 μm, avoiding the surrounding of the optic disc as much as possible. The sections were parallel to the sagittal plane of the cornea to the optic disc. 10 sections were randomly selected from each eyeball to be stained with hematoxylin and eosin, and the nucleus of vascular endothelial cells that broke through the inner limiting membrane of the retina was counted (only the nucleus of vascular endothelial cells closely related to the inner limiting membrane were counted), and the average number of cells per section per eyeball was counted.

Results: no or few nucleus of vascular endothelial cells that broke through the inner limiting membrane of the retina into the vitreous body was found in the control group. More nucleuses of vascular endothelial cell that broke through the inner limiting membrane of the retina were found in the model group, some of which appeared alone, some clustered, and some nucleuses of vascular endothelial cells were found to be adjacent to the deep retinal vessels on some sections, confirming that they were originated from the retina instead of the vitreous body or other tissues in eyes. Only a few nucleuses of vascular endothelial cell that broke through the inner limiting membrane of the retina were found in the sections of the treatment group. The experimental results are shown in Table 22.

TABLE 22

Nucleus count of vascular endothelial cells in each group

| Group | Dose (μg) | Nucleus number |
|---|---|---|
| Protein I | 100 | 6.693 ± 2.109 |
| Protein II | 100 | 7.333 ± 1.263 |
| Model group | — | 28.392 ± 2.220 |
| control | — | 1.315 ± 0.321 |

The results showed that the nucleus counts of retinal vascular endothelial cells in the fusion proteins I and II treatment groups were 6.693±2.109 and 7.333±1.263, compared with the oxygen model group (28.392±2.220), the nucleus counts of retinal vascular endothelial cells were significantly reduced, which proved that they can inhibit the neovascularization in the oxygen-induced neonatal rat retinopathy model to a certain extent.

Example 19

Effect of Fusion Proteins I and II on Neovascularization in Diabetic Retinopathy Rat Model The experimental diabetic rat model was established with streptozotocin STZ. STZ was dissolved in 0.1 mol/L citrate buffer at pH 4.5 to prepare a 2% solution. All experimental Wistar rats were fasted for 12 h before injection, and each rat was intraperitoneally injected with a 2% STZ solution at a dose of 65 mg/kg. After the injection, the rats were fed in single cages, and urine sugar and blood sugar were detected at the 48th. When urine sugar was +++ or above, and blood glucose was higher than 16.7 mmol/L, the model establishment requirement is reached. The diabetic retinopathy model was successfully established by detecting blood glucose, urine glucose and urine volume detection and retinal VEGF immunohistochemistry.

15 rats were randomly divided into three groups, which were labeled as a control group, a fusion protein I treatment group and a fusion protein II treatment group. The administration was performed via intravitreal injection once every 5 days for 2 weeks, in which the control group was injected with physiological saline (0.1 mL), and the fusion protein I and protein II were all administered with 100 μg (0.1 mL). Observation was performed on week 4, week 8, and week 12. The experimental results are shown in Table 23.

TABLE 23

Effect of protein I and protein II on neovascularization in a diabetic retinopathy rat model

| Group (n = 5) | Week 4 | Week 8 | Week 12 |
|---|---|---|---|
| Protein I | 182.03 ± 3.42 | 211.04 ± 3.33 | 252.36 ± 1.34 |
| Protein II | 188.26 ± 2.23 | 212.33 ± 4.59 | 257.92 ± 3.88 |
| control | 211.88 ± 4.36 | 227.52 ± 1.54 | 188.48 ± 3.89 |

The results showed that under an optical microscope, the number of ganglion cells in 10 retina of posterior pole in each eyeball was counted, and the thickness of 10 retina of posterior pole in each eyeball was measured. Compared with the control group, the thickness of each layer of the retinal tissue of the rats in the experimental group was increased. Compared with the control group, the number of ganglion cells in the retinal of rats in the experimental group was increased. Compared with the control group, the number of visual cells in the treatment group was increased. It was indicated that fusion proteins I and II could produce a certain therapeutic effect on diabetic retinopathy at 100 μg dose.

What is claimed is:

1. A fusion protein comprising: an antiangiogenesis polypeptide HM-3 sequence, an interleukin 4 (IL-4) peptide sequence and an Fc fragment sequence of a IgG1 antibody, wherein the HM-3 sequence, the interleukin 4 (IL-4) peptide sequence and the Fc fragment sequence of the IgG1 antibody are linked by linkers, and wherein the amino acid sequence of the fusion protein is SEQ ID NO: 1.

2. A fusion protein comprising: an antiangiogenesis polypeptide HM-3 sequence, an interleukin 4 (IL-4) peptide sequence and an Fc fragment sequence of a IgG1 antibody, wherein the HM-3 sequence, the interleukin 4 (IL-4) peptide sequence and the Fc fragment sequence of the IgG1 antibody are linked by linkers, and wherein the amino acid sequence of the fusion protein is SEQ ID NO: 2.

3. A DNA encoding the fusion protein according to claim 1, wherein the DNA comprises the SEQ ID NO: 3.

4. A DNA encoding the fusion protein according to claim 2, wherein the DNA comprises the SEQ ID NO: 4.

5. A method of treating rheumatoid arthritis, eye vascular diseases and/or retinopathy, comprising preparing a medicament comprising the fusion protein according to claim 1, and administering the medicament to a subject in need thereof at a pharmaceutically acceptable dosage.

* * * * *